(12) United States Patent
Lewis

(10) Patent No.: US 7,815,851 B1
(45) Date of Patent: Oct. 19, 2010

(54) STEAM STERILIZATION SYSTEM FOR STERILIZING MEDICAL WASTE

(76) Inventor: Robert W. Lewis, 9811 Warwick Cir., Charlotte, NC (US) 28210

( * ) Notice: Subject to any disclaimer, the term of this patent is extended or adjusted under 35 U.S.C. 154(b) by 1190 days.

(21) Appl. No.: 11/403,670

(22) Filed: Apr. 13, 2006

(51) Int. Cl.
*A61L 2/07* (2006.01)

(52) U.S. Cl. .............................. 422/3; 422/26

(58) Field of Classification Search ........................ None
See application file for complete search history.

(56) References Cited

U.S. PATENT DOCUMENTS

| | | | | |
|---|---|---|---|---|
| 5,251,825 A | * | 10/1993 | Dumaine et al. ............... | 241/16 |
| 5,340,536 A | * | 8/1994 | Datar et al. .................... | 422/23 |
| 6,867,393 B1 | * | 3/2005 | Lewis .......................... | 219/401 |
| 2004/0258559 A1 | * | 12/2004 | Paskal et al. .................. | 422/26 |

* cited by examiner

*Primary Examiner*—Elizabeth L McKane
(74) *Attorney, Agent, or Firm*—John F. A. Earley, III; Frank J. Bonini, Jr.; Harding, Earley, Follmer & Frailey, P.C.

(57) ABSTRACT

An integrated sterilization and materials handling system for sterilizing and handling items such as medical waste, paper, or other things comprises a cart for carrying a removable bin for holding the items to be sterilized, and a sterilization chamber that receives the bin when it is removed from the cart. The various embodiments include a bin that is dumpable with the cart using existing dumping apparatus, a bin that pivots on the cart to permit dumping of the items from the bin by tilting the bin, and a bin used primarily in a dry heat sterilization process of the invention when sterilizing items that are not to be discarded after sterilization to facilitate loading and unloading of the bin. The system has thermal energy booster plates mounted in the sterilization chamber for providing dry radiant heat to the chamber, and the system may vary process times, process pressures, and process temperatures to predetermine settings that correlate to the weight of the items to be sterilized.

23 Claims, 18 Drawing Sheets

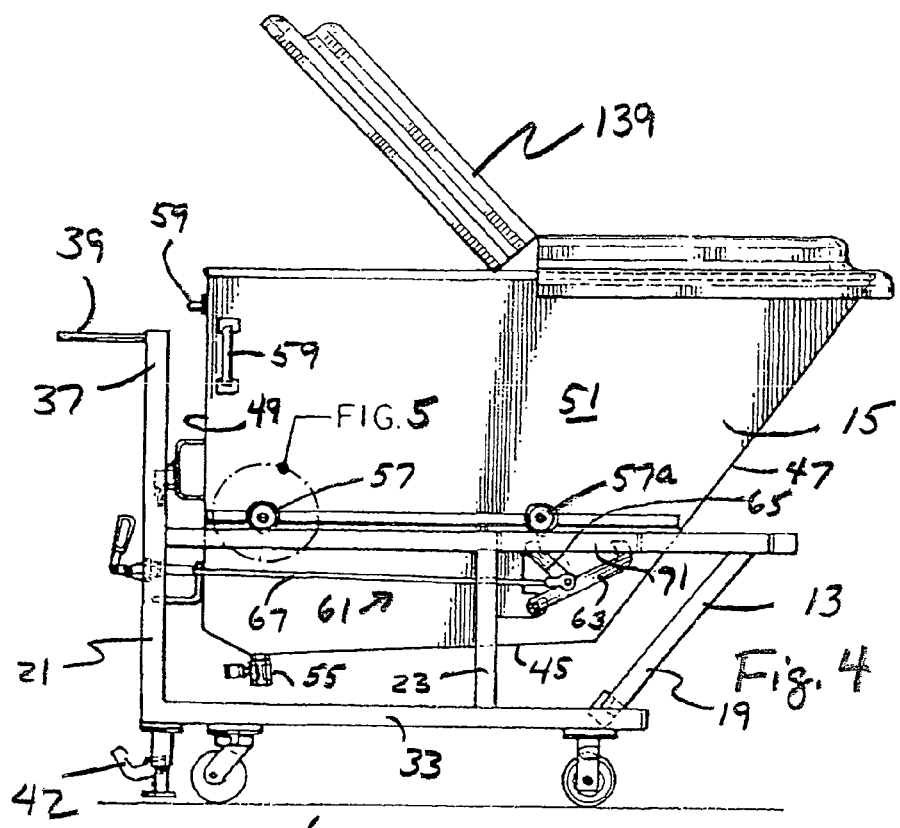
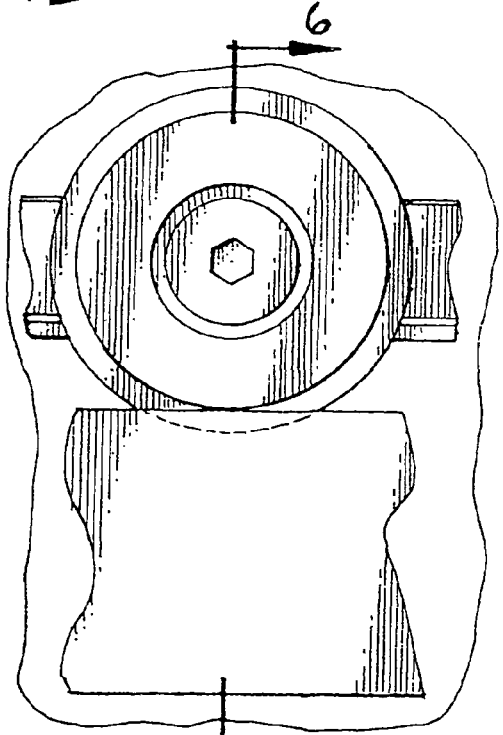
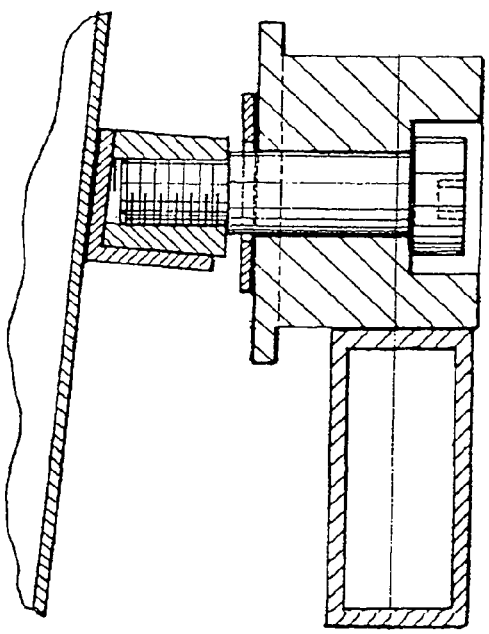
Fig. 4
Fig. 5
Fig. 6

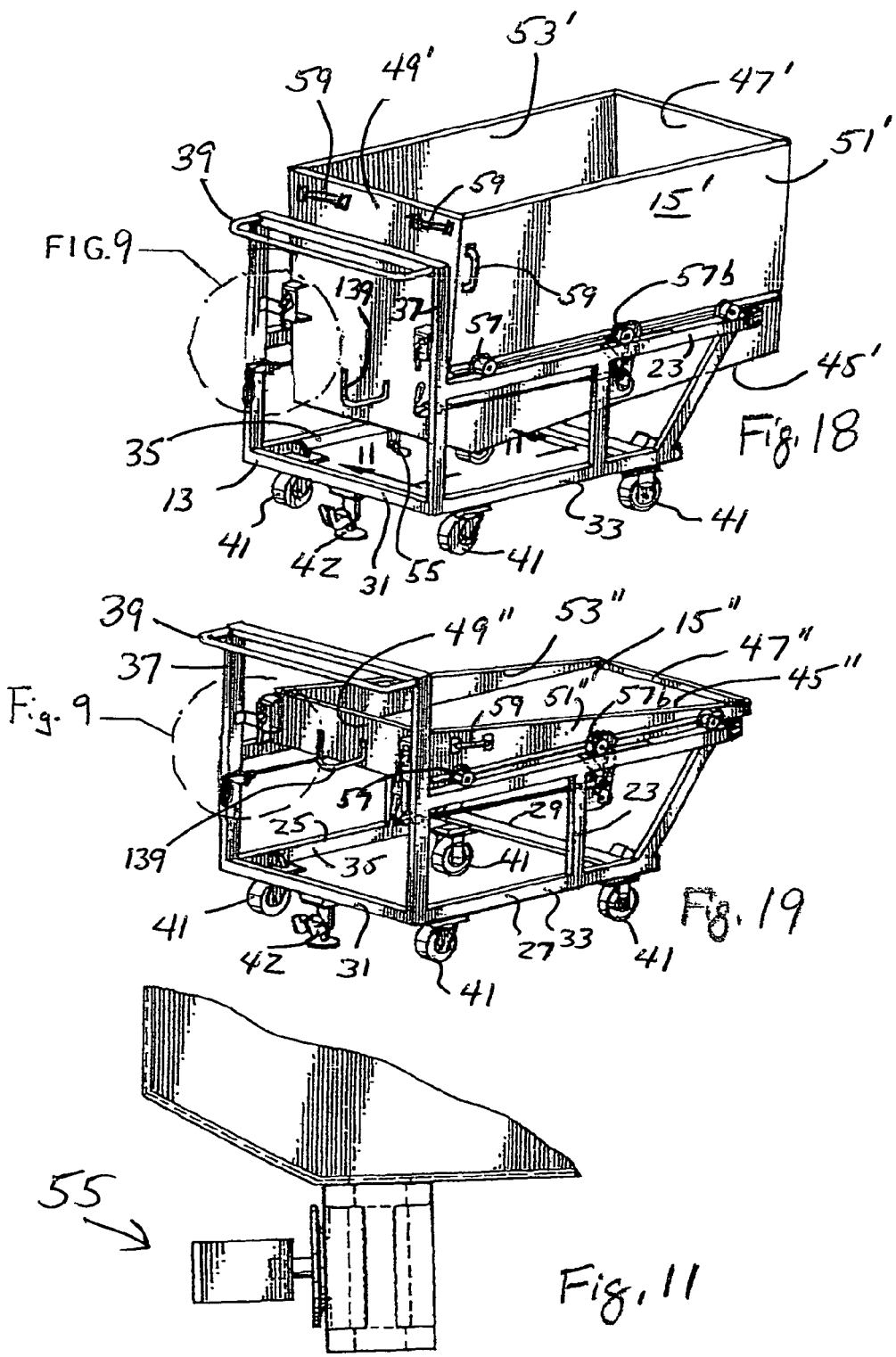

Valve Identification Table

| Valve Number | Valve Name | Type | Normal Position (Ready, Unpowered) |
|---|---|---|---|
| MS-1 | Main Steam Valve 105 | Electric Solenoid | Normally Closed |
| AS-2 | Auxiliary Steam Valve 108 | Electric Solenoid | Normally Closed |
| MV-3 | Main Vent Valve 117 | Electric Solenoid | Normally Open |
| AI-4 | Air Inlet Valve 153 | Electric Solenoid | Normally Open |
| D-5 | Drain Valve 101 | Electric Solenoid | Normally Closed |
| VS-6 | Vacuum Pump Suction Valve 113 | Electric Solenoid | Normally Closed |
| VD-7 | Vacuum Pump Discharge Valve 114 | Electric Solenoid | Normally Closed |
| WS-8 | Water Spray Valve cool-down 122 | Electric Solenoid | Normally Closed |
| WS-9 | Water Spray Valve Wash 123 | Electric Solenoid | Normally Closed |
| WSF-10 | Water Spray Manual Flow Control Valve 124 (Cool-down) | Flow Control | Normally Partially Open |
| WSF-11 | Water Spray Manual Flow Control Valve 125 (Wash) | Flow Control | Normally Partially Open |
| IV-12 | Steam Trap Isolation Valve Inlet | Ball | Normally Open |
| IV-13 | Steam Trap Isolation Valve Outlet | Ball | Normally Open |
| ST14 | Steam Trap | Inverted Bucket | Operates independantly |
| VWS-15 | Vacuum Pump Water Seal Valve 121 | Electric Solenoid | Normally Closed |
| VWS-16 | Vacuum Pump Water Seal Manual Flow Control Valve 126 | Flow Control | Normally Partially Open |

Fig. 14

Three Phase Process Cycle Detail (Wet & Dry Cycles) [Typical time settings in seconds]

| Wet Cycle Elapsed Time (sec) | Wet Cycle Variable Duration(sec) | Dry Cycle Elapsed Time (sec) | Dry Cycle Variable Duration(sec) | Step # | Automated Process | Process Description | Operator Action/Input | Display Description |
|---|---|---|---|---|---|---|---|---|
| | | | | 0 | Radiation Background Monitoring | | Door Is Open Operator Positions Cart | RealTime, Position Cart Enter User ID |
| | | | | 1 | Begin Cycle Data Acquisition Radiation Monitoring of load Capture & Calculate Weight of load | | Operator Enters user ID | |
| | | | | 2 | | | | Time of Day (TOD), Load Bin Open Bin Drain Valve, Close and Seal Door |
| | | | | 3 | Door Sensor made | | Operator Loads Bin, OpensBin Drain Valve and Closes & Seals Door | |
| | | | | 4 | Variable Timer settings automatically adjusted. | | Operator Selects cycle type (3Phase DRY, 3 Phase WET) | RealTime, SelectCycle, 3 Phase DRY, 3 Phase WET, Document, Wash |
| 1 | 1 | 1 | 1 | 5 | | | Operator press cycle start | RealTime, Load Weight, Cycle Start |
| | | | | | | Phase ONE | | |
| 2 | 1 | 2 | 1 | 6 | Door Latches Air Inlet (AI-4) - Closes | Thermal Energy Booster Plate steam remains open through entire Cycle | Automated Process Operator Elsewhere | Phase ONE, TOD, Replacing Air in Vessel with Steam, Pressure and Temp Display, Reload at TOD |
| 3 | 1 | 3 | 1 | 7 | Auxillary Steam (AS-2) Opens Opens | | | |
| 23 | 20 | 23 | 20 | 8 | Main Steam (MS-1) Opens Time Delay (1) | Gravity Steam Displaces Air | | |
| 28 | 5 | 28 | 5 | 9 | Main Vent (MV-3) Closes Temp Reaches 250F Press Reaches 17psig | | | |
| 628 | 600 | 628 | 600 | 10 | Time Delay (2) | Steam Soak, Airborne Pathogens | Automated Process Operator Elsewhere | Phase ONE, TOD, Treating Airborne Pathogens, Pressure and Temp Display, Reload at TOD |
| 629 | 1 | 629 | 1 | 11 | Main Steam (MS-1) Closes | | | |
| 630 | 1 | 630 | 1 | 12 | Main Vent (MV-3) Opens Time Delay (7) | Steam pressure Released to Atmosphere | | |
| 640 | 10 | 640 | 10 | 13 | Press Reaches to 0psig Drain (D-5) Opens Time Delay (3) | | | |
| 660 | 20 | 660 | 20 | 14 | Main Vent (MV-3) Closes Drain (D-5) Closes | Condensate Drains | | |
| 661 | 1 | 661 | 1 | 15 | Vacuum Suction (VS-6) Opens | | | |
| 662 | 1 | 662 | 1 | 16 | Vacuum Discharge (VD-7) Opens Vacuum Water Seal (VWS-15) Opens Vacuum Pump Starts | | Automated Process Operator Elsewhere | Phase ONE, TOD, Vacuum Cycle # 1, Pressure and Temp Display, Reload at TOD |
| 1142 | 480 | 1142 | 480 | 17 | Vacuum Reaches 28inHG Time Delay (4) | Vacuum Draw | | |
| 1162 | 20 | 1202 | 60 | 18 | Vacuum Suction (VS-6) Closes Vacuum Pump Stops | Vacuum Hold | | |
| 1163 | 1 | 1203 | 1 | 19 | Vacuum Water Seal (VWS-15) Closes | | | |
| 1164 | 1 | 1204 | 1 | 20 | Vacuum Discharge (VD-7) Closes | | | |

Fig. 15a

Three Phase Process Cycle Detail (Wet & Dry Cycles) [Typical time settings in seconds]

| Wet Cycle Elapsed Time (sec) | Wet Cycle Variable Duration(sec) | Dry Cycle Elapsed Time (sec) | Dry Cycle Variable Duration(sec) | Step # | Automated Process | Process Description | Operator Action/Input | Display Description |
|---|---|---|---|---|---|---|---|---|
| | | | | | Phase TWO | | | |
| 1169 | 5 | 1224 | 20 | 21 | Main Steam (MS-1) Opens<br>Pressure Reaches 17psig<br>Temp Reaches 250F | Steam Replaces Vacuum | Automated Process<br>Operator Elsewhere | Phase TWO, TOD, Disinfection Cycle,<br>Pressure and Temp Display, Reload at TOD |
| 8369 | 7200 | 3924 | 2700 | 22 | Time Delay (5)(6) | Disinfection of Waste, Timer 5 for DRY Cycle, Timer 6 for WET Cycle | | |
| 8374 | 5 | 3929 | 5 | 23 | Main Steam (MS-1) Closes<br>Main Vent (MV-3) Opens<br>Pressure Reaches 0psig | Vent Steam to Atmosphere | | |
| 8384 | 10 | 3939 | 10 | 24 | Time Delay (7)<br>Drain (D-5) Opens | | | |
| 8444 | 60 | 3999 | 60 | 25 | Time Delay (8)<br>Drain (D-5) Closes<br>Main Vent (MV-3) Closes | Drain Condensate | | |

Fig. 15b

Three Phase Process Cycle Detail (Wet & Dry Cycles) [Typical time settings in seconds]

| Wet Cycle Elapsed Time (sec) | Wet Cycle Variable Duration(sec) | Dry Cycle Elapsed Time (sec) | Dry Cycle Variable Duration(sec) | Step # | Automated Process | Process Description | Operator Action/Input | Display Description |
|---|---|---|---|---|---|---|---|---|
| | | | | | Phase THREE | | | |
| 8445 | | 4000 | | 26 | Vacuum Suction (VS-6) Opens | | | |
| 8446 | 1 | 4001 | 1 | 27 | Vacuum Discharge (VD-7) Opens Vacuum Water Seal (VWS-15) Opens | | Automated Process Operator Elsewhere | Phase THREE, TOD, Vacuum Cycle # 2, Pressure and Temp Display, Reload at TOD |
| 8926 | 480 | 4481 | 480 | 28 | Vacuum Pump Starts Vacuum Reaches 28inHG | | | |
| 9526 | 600 | 4781 | 300 | 29 | Time Delay (9)(10) | Vacuum Draw Vacuum Hold, liquid vaporization, Timer 9 for DRY Cycle, Timer 10 for WET Cycle | | |
| 9527 | 1 | 4782 | 1 | 30 | Vacuum Suction (VS-6) Closes Vacuum Pump Stops Vacuum Water Seal (VWS-15) Closes | | | |
| 9527 | 1 | 5682 | | | | | | |
| 9528 | 1 | 5683 | 1 | 31 | Vacuum Discharge (VD-7) Closes | | | |
| 9529 | 1 | 5684 | 1 | 32 | Auxiliary Steam (AS-2) Closes | Thermal Energy Booster Plate Closes | | |
| 9539 | 10 | 5694 | 10 | 33 | Air Inlet (AI-4) opens Pressure reaches 0psig | | | |
| 9540 | 1 | 5695 | 1 | 34 | Main Vent (MV-3) Opens | | Automated Process Operator Elsewhere | Phase THREE, TOD, Cool Down, Pressure and Temp Display, Reload at TOD |
| 9541 | 1 | 5696 | 1 | 35 | Air Inlet (AI-4) Closes Drain (D-6) Opens | | | |
| 9841 | 300 | 5996 | 300 | 36 | Water Spray (WS-8) Opens Temp reaches 100F | | | |
| 9851 | 10 | 6006 | 10 | 37 | Time Delay (11) | Water Sprays on Cart | | |
| 9911 | 60 | 6066 | 60 | 38 | Water Spray (WS-8) Closes Time Delay (12) | | | |
| 9912 | 1 | 6067 | 1 | 39 | Air Inlet (AI-4) opens Drain (D-5) Closes | Additional Drainage Time | | |
| 9927 | 15 | 6082 | 15 | 40 | Print Cycle Report | Cycle Report Prints on Local Printer | Automated Process Operator Elsewhere | TOD,Printing Cycle Report |
| 9937 | 10 | 6092 | 10 | 41 | Export Cycle Report | Cycle Data exports to HD, YTD prcessing report updates | | TOD, Exporting Cycle Report |
| 9938 | 1 | 6093 | 1 | 42 | Door Latch Releases | | | Cycle Complete, Open Door, Close Bin Drain Valve and remove Bin |
| 9938 | | 6093 | | 43 | Door Sensor un-made | | Operator Opens door Operator Closes Bin Drain Valve Operator Removes Bin and Dumps Bin Back to Top | RealTime, Position Cart Enter User ID |
| 9938 | | 6093 | | 44 | | | | |

| ycle Time (min | 165.63 | 101.55 |
|---|---|---|
| CycleTime/hrs | 2.76 | 1.69 |

Fig. 15c

Automatic Variable Process Timer Setting Table [in seconds]

| Variable Timer # | Variable Timer Name | "Typical" Time Factor | "Typical" Baseline Setting for 90 Pounds (#), in seconds | "Typical" times for Load weight (from Scale, Gross Wght − Tare Wght) | | | | | | |
|---|---|---|---|---|---|---|---|---|---|---|
| | | | | 102 ※ | 114 ※ | 126 ※ | 150 ※ | 167 ※ | 200 ※ |
| 1 | Phase ONE Gravity Steam Timer | 2 | 20 | 44 | 68 | 92 | 140 | 174 | 240 |
| 2 | Phase ONE Steam Cycle Timer | 5 | 600 | 660 | 720 | 780 | 900 | 985 | 1150 |
| 3 | Phase ONE Drain Timer | 0.1 | 20 | 21 | 22 | 24 | 26 | 28 | 31 |
| 4 | Phase ONE Vacuum Timer | fixed | 5 | | | | | | |
| 5 | Phase TWO Steam Cycle Time DRY | 30 | 2700 | 3060 | 3420 | 3780 | 4500 | 5010 | 6000 |
| 6 | Phase TWO Steam Cycle Time WET | 30 | 7200 | 7560 | 7920 | 8280 | 9000 | 9510 | 10500 |
| 7 | Steam Vent Timer | fixed | 10 | | | | | | |
| 8 | Phase TWO Drain Timer | 0.1 | 60 | 61 | 62 | 64 | 66 | 68 | 71 |
| 9 | Phase THREE Vaccum Timer DRY | 15 | 300 | 480 | 660 | 840 | 1200 | 1455 | 1950 |
| 10 | PHASE THREE Vaccum Timer WET | 10 | 900 | 1020 | 1140 | 1260 | 1500 | 1670 | 2000 |
| 11 | Water Spray Timer | 0 | 100 | 100 | 100 | 100 | 100 | 100 | 100 |
| 12 | Phase THREE Drain Timer | 0.2 | 60 | 62 | 65 | 67 | 72 | 75 | 82 |
| 13 | Documement Heat Cycle Timer | 30 | 3600 | 3960 | 4320 | 4680 | 5400 | 5910 | 6900 |
| 14 | Wash Spray Timer | fixed | 120 | | | | | | |
| 15 | Wash Drain Timer | fixed | 300 | | | | | | |
| 16 | 3 Phase Process Pressure Rise Anticipation Timer | fixed | 10 | | | | | | |
| 17 | 3 Phase Process Temperature Rise Anticipation Timer | fixed | 60 | | | | | | |
| 18 | Document Process Temperature Rise Anticipation Timer | fixed | 600 | | | | | | |
| 19 | Process Vacuum Anticipation Timer | fixed | 600 | | | | | | |

This table is for demonstration purposes only and is "typical timer settings". The time factors are to be determined during System Set-Up

Fig. 16

Wash Cycle Detail [typical time settings in seconds]

| Elapsed Time (sec) | Duration (sec) | Step # | Automated Process | Process Description | Operator Action/Input | Display Description |
|---|---|---|---|---|---|---|
| | | 0 | | | Door is Open | TOD, Position Cart Enter User ID |
| | | 1 | Radiation Background Monitoring | | Operator Positions Cart | |
| | | 2 | Begin Cycle Data Acquisition Radiation Monitoring of load Capture & Calculate Weight of load | | Operator Enters user ID | TOD, Load Bin Open Bin Drain Valve, Close and Seal Door |
| | | 5 | Door Sensor made | | Operator Loads Bin, Opens Bin Drain Valve and Closes & Seals Door | |
| | | 6 | Abandon Cycle Data Acquisition, Count Wash Cycle | | Operator Selects cycle type (Wash) | TOD, SelectCycle, 3 Phase WET, 3 Phase DRY, Document, Wash |
| 1 | 1 | 7 | | | Operator press cycle start | TOD, DRY,WET,WASH Cycle Start PB |
| 2 | | 8 | Door Latches Air Inlet (AI-4) Closes | | | |
| 3 | 1 | 10 | Auxiliary Steam (AS-2) Opens | Thermal Energy Booster Plate steam remains open through entire Cycle | | |
| 4 | 1 | 11 | Drain (D-5) Opens | | | |
| 5 | 1 | 12 | Water Spray (WS-9) Opens Time Delay (14) | | | |
| 65 | 60 | 14 | Water Spray (WS-9) Closes Time Delay (15) | Wash Water Sprays on Cart | Automated Cycle Operator Elsewhere | TOD, Bin Washing in Progress, Pressure and Temp Display, Reload at TOD |
| 65 | | | | | | |
| 365 | 300 | 15 | Drain (D-5) Closes | | | |
| 365 | | 17 | Auxiliary Steam (AS-2) Closes | Thermal Energy Booster Plate Closes | | |
| 366 | 1 | 18 | Air Inlet (AI-4) opens | | | |
| 367 | | 19 | Pressure reaches 0psig Temp reaches 100F | Safety Limits, Cooling by convection | | |
| 367 | | | | | | |
| 367 | | | | | | |
| 368 | 1 | 20 | Door Latch Releases | | | TOD, Cycle Complete, Open Door, Close Bin Drain Valve and remove Bin |
| 368 | | 21 | Door Sensor un-made | | Operator Opens door Operator Closes Bin Drain Valve Operator Removes Bin Back to Top | TOD, Position Cart, Enter User ID |
| 368 | | 23 | | | | |
| 368 | | 24 | | | | |
| 6.13 | Cycle Time (mins) | | | | | |
| 0.10 | CycleTime(hrs) | | | | | |

Fig. 17

Document Cycle Detail [Typical time settings in seconds]

| Elapsed Time (sec) | Duration (sec) | Step # | Automated Process | Process Description | Operator Action/Input | Display Description |
|---|---|---|---|---|---|---|
| | | 0 | | | Door is Open | TOD, Position Cart Enter User ID |
| | | 1 | Radiation Background Monitoring | | Operator Positions Cart | |
| | | 2 | Begin Cycle Data Acquisition Radiation Monitoring of load Capture & Calculate Weight of load | | Operator Enters user ID | TOD, Load Bin Open Bin Drain Valve, Close and Seal Door |
| | | 5 | Door Sensor made | | Operator Loads Bin, OpensBin Drain Valve and Closes & Seals Door | |
| | | 6 | Variable Timer settings automatically adjusted | | Operator Selects cycle type (Document) | TOD, SelectCycle, 3 Phase WET, 3 Phase DRY, Document, Wash |
| 1 | 1 | 7 | | | Operator press cycle start | TOD, Cycle Start PB |
| 2 | 1 | 8 | Door Latches Air Inlet (AI4) - Closes Min Vent (MV-3) Closes | | | |
| 3 | 1 | 10 | Auxiliary Steam (AS-2) Opens | Thermal Energy Booster Plate steam remains open through entire Cycle | | |
| 4 | 1 | 11 | Temperature reaches SP Time Delay (13) | | | |
| 3604 | 3600 | | | | | |
| 3605 | 1 | 12 | Auxiliary Steam (AS-2) Closes | Thermal Energy Booster Plate Closes | Automated Cycle Operator Elsewhere | TOD, Bin Washing in Progress, Pressure and Temp Display, Reload at TOD |
| 3606 | 1 | 14 | Air Inlet (AI4) opens | | | |
| 3607 | 1 | 15 | Min Vent (MV-3) Opens | | | |
| 4207 | 600 | 16 | Pressure reaches 0psig | | | |
| 4207 | | 17 | Temp reaches 100F | Safety Limits, Cooling by convection | | |
| 4208 | 1 | 18 | Door Latch Releases | | | TOD, Cycle Complete, Open Door, Close Bin Drain Valve and remove Bin |
| 4208 | | 19 | Door Sensor un-made | | Operator Opens door | |
| 4208 | | 20 | | | Operator Closes Bin Drain Valve | |
| 4208 | | 21 | | | Operator Removes Bin Back to Top | TOD, Position Cart, Enter User ID |
| 70.13 | Cycle Time (mins) | | | | | |
| 1.17 | Cycle Time (hrs) | | | | | |

Fig. 20

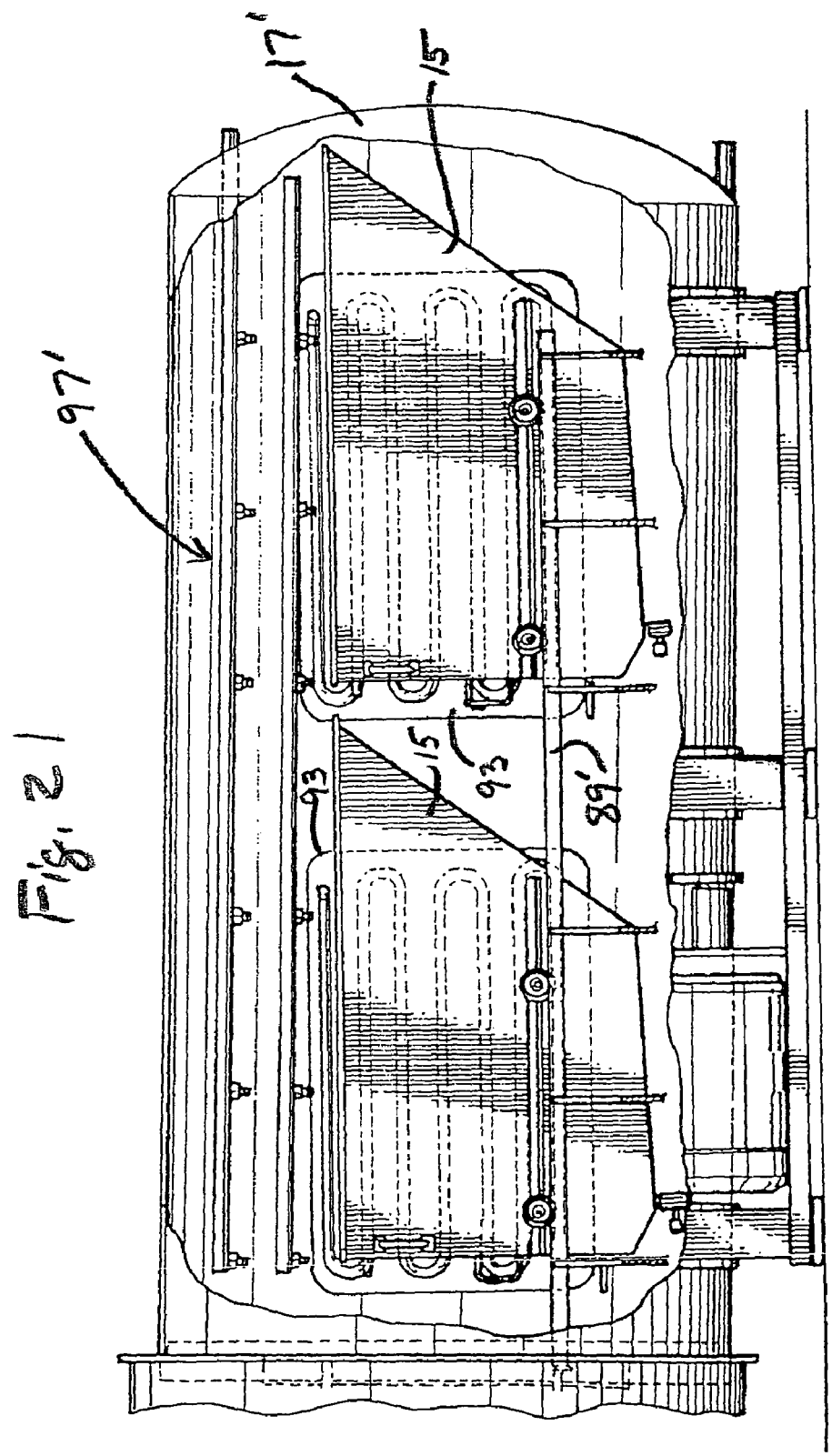

Variable Timer Identification Table

| Variable Timer # | Name | Type | Description |
|---|---|---|---|
| 1 | Phase ONE Gravity Steam Timer | Automatic, Variable | Phase ONE, Time to allow for steam to fill chamber by gravity |
| 2 | Phase ONE Steam Cycle Timer | Automatic, Variable | Phase ONE, Time to Soak for Airborne Pathogen Kill |
| 3 | Phase ONE Drain Timer | Automatic, Variable | Phase ONE, Time to hold drain open for Condensate. |
| 4 | Phase ONE Vacuum Timer | Set at Validation | Phase ONE, Time to hold vacuum |
| 5 | Phase TWO Steam Cycle Time DRY | Automatic, Variable | Phase TWO, DRY, Time to Steam Soak for Sterilization |
| 6 | Phase TWO Steam Cycle Time WET | Automatic, Variable | Phase TWO, WET, Time to Steam Soak for Sterilization |
| 7 | Steam Vent Timer | Set at Validation | Phase ONE & TWO, Time to allow for Steam & Pressure to vent. |
| 8 | Phase TWO Drain Timer | Automatic, Variable | Phase TWO, Time to hold drain open for Condensate |
| 9 | Phase THREE Vaccum Timer DRY | Automatic, Variable | Phase THREE, DRY, Time hold hold vacuum for vaporization |
| 10 | Phase THREE Vacuum Timer WET | Automatic, Variable | Phase THREE, WET, Time hold hold vacuum for vaporization |
| 11 | Coolong Water Spray Timer | Automatic, Variable | Phase THREE, Time to spray Bin for Cool-down |
| 12 | Phase THREE Drain Timer | Automatic, Variable | Phase THREE, Time to hold drain open for Condensate |
| 13 | Documenent Heat Cycle Timer | Automatic, Variable | Document Sterilization, Time to hold at temperature for Sterilization |
| 14 | Wash Spray Timer | Set at Validation | Wash Cycle, Time to spray |
| 15 | Wash Drain Timer | Set at Validation | Wash Cycle, Time to hold drain open |
| 16 | 3 Phase Process Pressure Rise Anticipation Timer | Set at Validation | FAULT, Time to wait for Pressure Rise before Fault notification |
| 17 | 3 Phase Process Temperature Rise Anticipation Timer | Set at Validation | FAULT, 3 Phase Process, Time to wait for Temperature Rise before Fault notification |
| 18 | Document Process Temperature Rise Anticipation Timer | Set at Validation | FAULT, Document Process, Time to wait for Temperature Rise before Fault notification |
| 19 | Process Vacuum Anticipation Timer | Set at Validation | FAULT, Time to wait for Vacuum Rise before Fault notification |

Fig. 23

STEAM STERILIZATION SYSTEM FOR STERILIZING MEDICAL WASTE

BACKGROUND OF TEE INVENTION

1. Field of the Invention

This invention relates to a steam sterilization system for sterilization of items such as regulated medical waste, and more particularly concerns a steam sterilization system that integrates material handling with the sterilization process to reduce handling and pathogen exposure.

2. Description of the Prior Art

Regulated medical waste generated by hospitals and the like is required to be sterilized prior to being disposed. Typically, plastic and/or rubber carts of approximately one cubic yard in size are used in hospitals to collect medical waste which has been placed in waste containment systems (i.e., sharps containers, sealed red plastic bags, etc.). The plastic/rubber carts are used to collect and to haul the containment systems containing the medical waste to the hospital's sterilization unit, where the waste containment systems containing the medical waste are unloaded from the cart and placed into the sterilization unit to be sterilized. After sterilization, the waste containment systems containing the now sterilized medical waste are transferred back onto the cart and conveyed to typically a solid waste compactor unit for final disposal, generally, in a sanitary landfill.

Sterilization units that are based upon steam sterilization generally have a drawback of water condensation from the steam forming on the treated medical waste, which increases the weight of the treated medical waste and therefore the cost of the disposing of the treated medical waste in a landfill.

Sterilization units based upon a vacuum autoclave have the drawback of potentially pumping airborne pathogens out of the vacuum autoclave into the environment during a sterilization process. This leads to potential contamination or alternatively to higher costs in providing filtration systems/ventilators for treating the airborne pathogens being pumped out of the vacuum autoclave.

U.S. Pat. No. 6,867,393, which is incorporated herein by reference, discloses a steam sterilization system for sterilizing medical waste and a method of sterilizing medical waste that uses the combination of steam and vacuum. The system comprises a cart for carrying a removable bin for holding medical waste, and a sterilization chamber that receives the bin when it is removed from the cart. The bin may be rolled from the cart and rolled into the chamber along respective rail assemblies on the cart and in the chamber, where the medical waste in the bin is sterilized, and upon completion of the sterilization process, the bin may be rolled from the chamber back onto the cart and transported by the cart to a dumping location.

SUMMARY OF THE INVENTION

It is an object of the invention to provide a sterilization system for sterilizing items such as regulated medical waste.

Another object of the invention is to provide a sterilization system that avoids the condensation drawback of known steam based sterilization units as well as the airborne pathogen drawback of known vacuum autoclave systems.

Another object of the invention is to provide a sterilization system that provides the efficacy of a vacuum based sterilization system without the airborne pathogen drawback mentioned above.

Still another object of the invention is to provide a sterilization system that integrates material handling with the sterilization process, thereby reducing handling and pathogen exposure.

Another object of the invention is to refine and expand on the sterilization system and the sterilization method disclosed in U.S. Pat. No. 6,867,393.

These and other objects are accomplished by my invention which is set out below.

BRIEF DESCRIPTION OF THE DRAWINGS

FIG. 4 is a view in side elevation of the cart and the bin of FIGS. 1-3, with the latching assembly 61 disengaged from the front wheels 57a of the bin 15;

FIG. 5 is an enlarged view of wheel 57 of the bin 15 riding on the rail 44 of the cart rail assembly 43 shown in the circle 5 of FIG. 4;

FIG. 6 is a view taken along the lines and arrows 6-6 of FIG. 5;

FIG. 11 is a view in partial cross-section taken along the lines and arrows 11-11 of FIG. 18;

FIG. 14 is a chart identifying the valves used in the system of the invention;

FIGS. 15a, 15b, and 15c combined show a chart illustrating the three phase sterilization process of the invention with example settings;

FIG. 16 is chart providing illustrative parametric settings for various load weights of items to be sterilized;

FIG. 17 is a chart illustrating the wash cycle of the invention with example settings;

FIG. 18 is a view in perspective showing an alternative embodiment of the bin removably mounted on the cart;

FIG. 19 is a view in perspective showing another alternative embodiment of the bin removably mounted on the cart;

FIG. 20 is a chart illustrating the dry sterilization process of the invention with example settings;

FIG. 21 is a view in side elevation showing an alternative embodiment of the sterilization chamber, with a cutaway of the chamber wall to illustrate the interior of the chamber;

FIG. 23 is a chart identifying various variable timers that may be used in preferred embodiments of the invention.

DETAILED DESCRIPTION

Figure 1:
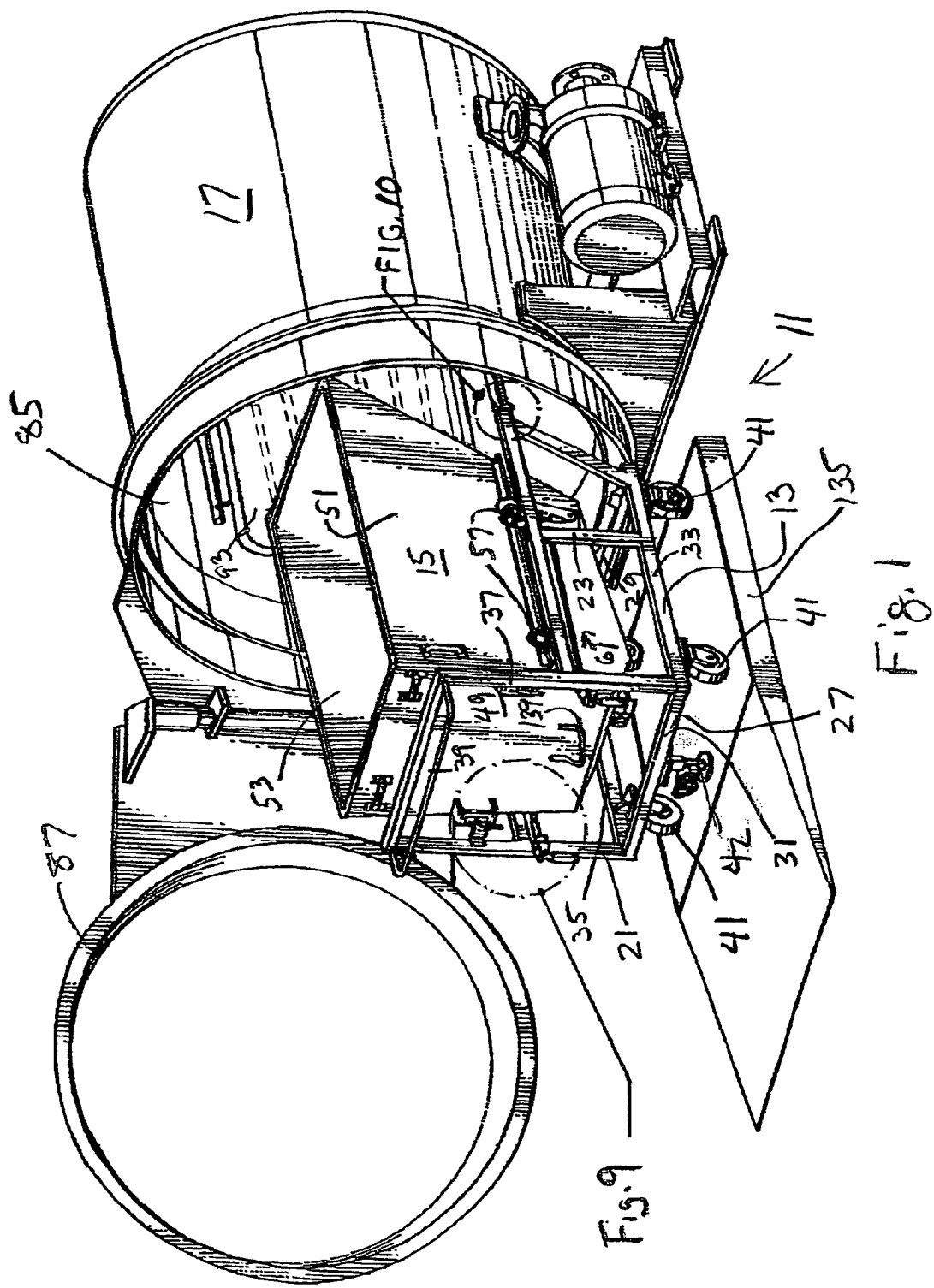
FIG. 1 is a view in perspective of a sterilization system constructed in accordance with the invention, showing a removable bin for holding items (such as medical waste) to be sterilized just prior to being rolled from a cart which has been positioned before a sterilization chamber, into the sterilization chamber for commencement of a sterilization process to sterilize the items to be sterilized in accordance with the invention.

Turning to the drawings, there is shown a steam sterilization system 11 for sterilizing medical waste. In this preferred embodiment of the invention, the steam sterilization system 11 comprises a cart 13, a bin 15 for holding medical waste, the bin 15 being removably mountable to the cart 13, and a sterilization chamber 17.

As shown in drawings, and particularly in FIGS. 1-4, 7, and 12, the cart 13 for carrying the removable bin 15 has a front end portion 19, a rear end portion 21, and two side end portions 23, 25. The cart 13 has a rectangular-shaped base frame portion 27 having a pair of cross beams 29 and 31 extending between the side beams 33, 35. The cart 13 also includes a handle support frame portion 37 extending upwardly from the base frame portion 27 at the rear end portion 21 of the cart 13, and a handle assembly 39 is mounted onto the handle support frame portion 37 to facilitate pushing of the cart 13. Preferably, the cart 13 is constructed of aluminum alloy to reduce weight, and is anodized to provide a corrosion resistant surface that is easily cleaned.

Wheels 41, preferably the rear two being castor wheels and the front two being fixed wheels, are mounted on the underside of the base frame portion 27 of the cart 13 to provide mobility to the cart 13. Preferably, the wheels 41 have a 5" diameter and are made of polyethylene, so as to provide smooth handling over various surfaces and to not mark or damage finished flooring.

A floor brake 42 is mounted on the cross beam 31 of the frame portion 27 of the cart 13, and, when in an engaged position reached by being activated by foot pressure applied by a cart user, engages the floor to hold the cart 13 in place when unattended, when positioned at the chamber opening 85 for unloading of the bin 15 from the cart 13 to the chamber 17 or loading of the bin 15 from the chamber 17 to the cart 13, or when the bin 15 is to be dumped by tilting as described below after the items contained therein have been sterilized.

A rail assembly 43 is provided on each side beam 33, 35 of base frame portion 27 of the cart 13, and each rail assembly 43 has a rail 44.

As shown in the drawings, and particularly in FIGS. 1-4, 7, and 12, the bin 15 in this preferred embodiment of the invention has a bottom wall 45, and a front wall 47, a rear wall 49, and two side walls 51, 53 extending upwardly the bottom wall 45.

Preferably the bin 15 is fabricated from corrosion resistant stainless steel and has a 33⅞ inch width, a 59 inch length, and a height of about 36 inches, with an approximate usable volume of 1.25 cubic yards. The two side walls 51 and 53 of the bin 15 are angled in slightly from top to bottom, and the front wall 47 of the bin 15 is more dramatically angled in from top to bottom. A drain valve 55, preferably a ½ inch ball valve, is connected to the bottom wall 45 near the rear wall 49 of the bin 15 for permitting liquid to drain from the bin 15 when desired.

The bin 15 is provided with wheels 57, including front wheel 57a, mounted on each side wall 51, 53 of the bin 15. The wheels 57 are spaced such that the wheels 57 engage the rail assemblies 43 located on the side end portions 23 and 25 of the cart 13 so that the bin 15 may be rolled off the cart 13 along the rails 44 when the bin 15 is being loaded into the sterilization chamber 17 from the cart 13 and so that the bin 15 may be rolled onto the cart 13 along the rails 44 and 90 when the bin 15 is being loaded onto the cart 13 from the sterilization chamber 17 after sterilization.

Handle grips 59 are mounted on the rear wall 49 and on the side walls 51, 53 of the bin 15 to facilitate handling of the bin 15.

As shown in detail in FIGS. 4, 7, 8 and 9, a latching assembly 61 is provided on each side end portion of the cart 13 for latching the bin 15 to the cart 13, when desired. Each latching assembly 61 includes a pair of hook arms 63, 65 pivotally mounted on the cart 13 for engaging the front wheel 57a on the side of the bin 15 that the latching assembly 61 is located to prevent the bin 15, when it is positioned on the cart 13, from moving forward on the rail assemblies 43 of the cart 13 when it is desired to have the bin 15 secured to cart 13. A rod 67 is connected at one end to the hook arms 63 and 65, and at the other end to an actuator 69, which is used to move the rod 67 which thereby causes the hook arms 63 and 65 to pivot through a slot 71 formed in each rail assembly 43 into an engaged position around the wheel 57a or into a disengaged position shown in broken lines and double dots in FIG. 8.

Figure 9:
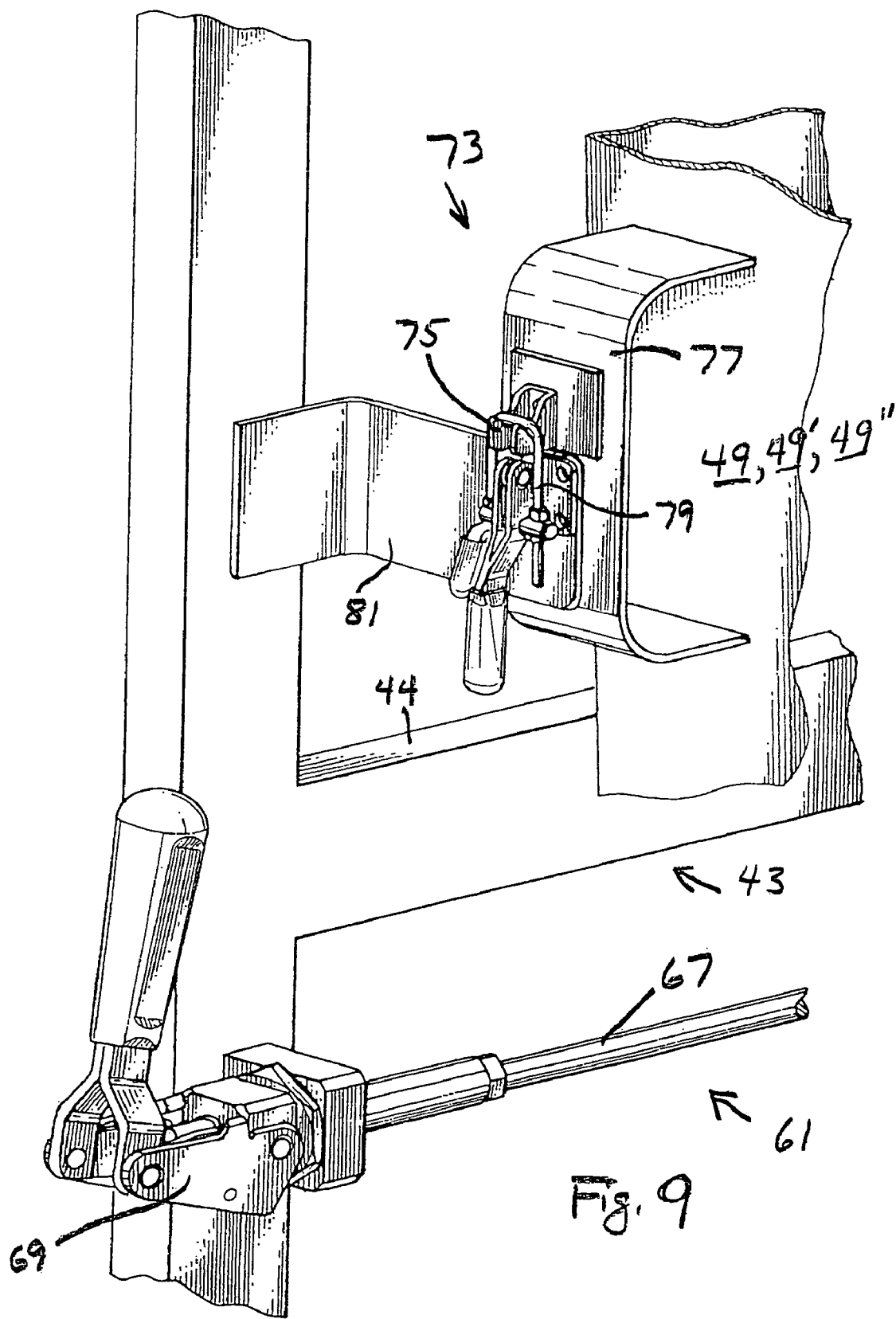
FIG. 9 is an enlarged view of the latching assembly 73 and the rod 67 and actuator 69 of the latching assembly 61 shown in the circle 9 of FIGS. 1, 18, and 19, except that the actuator 69 has been moved into a position placing the hook arms 63 and 65 into a disengaged (unlatched) position shown in FIG. 4.

As shown in the drawings, and particularly in FIG. 9, a pair of latching assemblies 73 also is provided. Each latching assembly 73 has a catch 75 mounted on a bracket 77 formed on the rear wall 49 of the bin 15, and a latching member 79 mounted on a bracket 81 on the cart 13. Latching apparatus 73 operates like a lunch box latching apparatus, with latching member 79 latching onto the catch 75 to prevent the bin 15 from rolling forward off the cart 13 and to prevent the rear end portion of the bin 15 from being lifted off the cart. The brackets 81 mounted on the cart 13 also act as a stop to prevent the bin 15 from rolling rearwardly on the rail assemblies 43 beyond the brackets 81.

Figure 2:
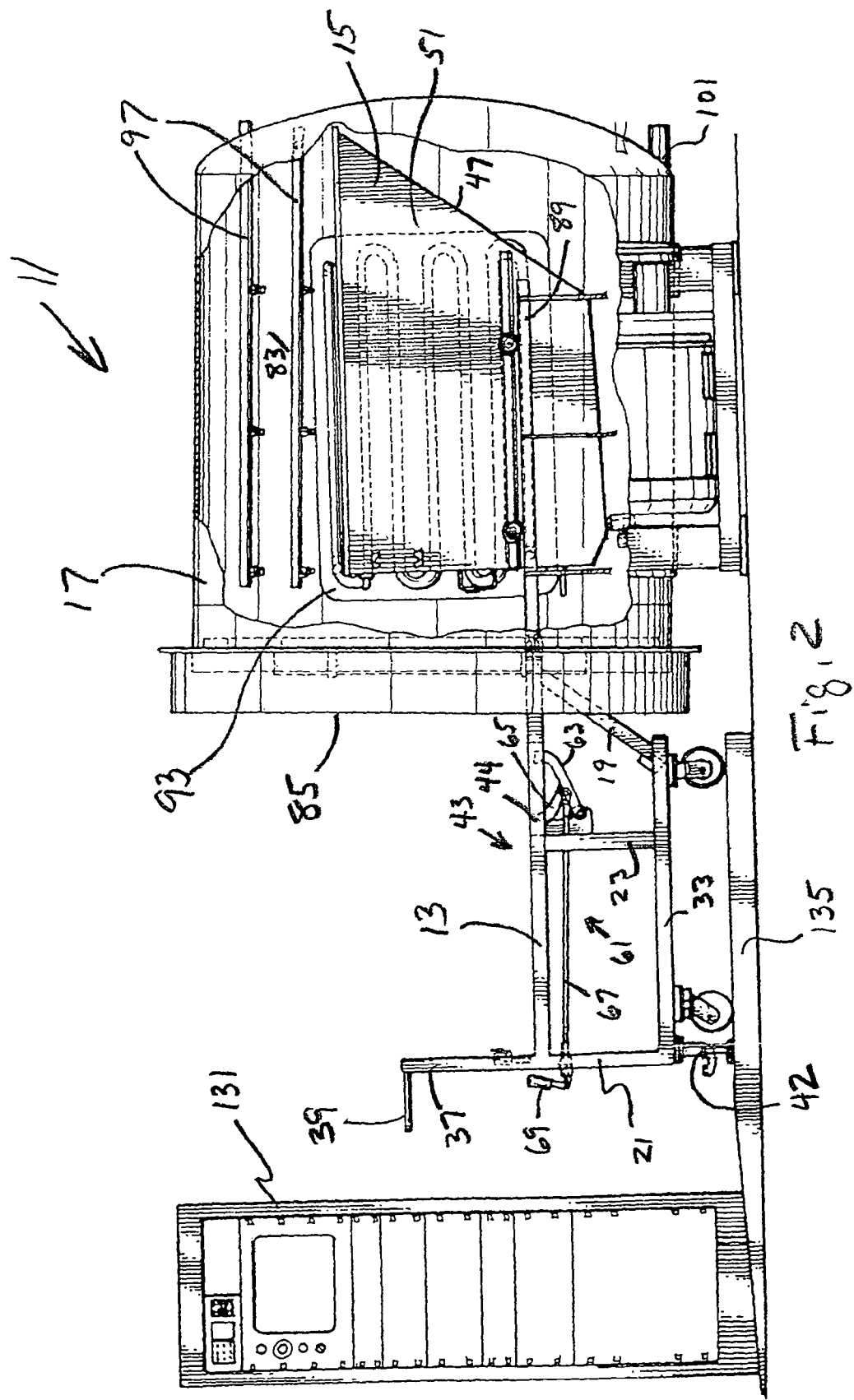
FIG. 2 is a view in side elevation of the system of FIG. 1, after the removable bin has been rolled into the sterilization chamber.

The sterilization chamber 17 has in interior 83 where sterilization takes place. The sterilization chamber 17 has an opening 85 through which access to the interior 83 of the sterilization chamber 17 is obtained, and the sterilization chamber 17 has a door 87 mounted at the opening 85 for sealingly closing the opening 85 against both pressure and vacuum when closed. The sterilization chamber 17 preferably is 60 inches in diameter and 64 inches long, and is constructed of corrosion resistant stainless steel. It is mounted on chamber support cradles and positioned at a convenient elevation for use in conjunction with the cart 13 and bin 15. The chamber 17 is sloped slightly downwardly from front to back to facilitate drainage. As shown in FIGS. 1 and 2, the door 87 preferably is a full opening hinged door that provides unobstructed access to the sterilization chamber 17 when the door 87 is fully opened. The door 87 preferably is equipped with either an automatic or manual latching mechanism to seal the door against both pressure and vacuum. Also, the door 87 preferably is equipped with safety innerlocks to prevent operation of the chamber 17 when the door 87 is ajar and to prevent opening the door until safe pressure and temperature conditions are restored.

Preferably, the sterilization chamber 17 is equipped with a pressure relief valve device to prevent over pressurization, and preferably, the sterilization chamber 17 is designed and constructed in accordance with the ASME, Code Section VIII, Division 1, and may receive an ASME "U" stamp as an unfired pressure vessel. The chamber 17 preferably at least meets Seismic Zone 3 specifications.

As shown in FIGS. 1 and 2, the sterilization chamber 17 is provided with a rail assembly 89 that is located in the interior 83 of the sterilization chamber 17. The rail assembly 89 has pair of parallelly spaced rails 90 on which the wheels 57 of the bin 15 ride when the bin 15 is inserted into the sterilization chamber 17 from the cart 13 prior to sterilization and on which the wheels 57 of the bin 15 ride when the bin 15 is being removed from the sterilization chamber 17 and rolled back onto the cart 13 via rail assemblies 43 after sterilization. Preferably, the rail assembly 89 is made of stainless steel.

To facilitate aligning the rails 44 of the rail assemblies 43 of the cart 13 with the rails 90 of the rail assembly 89 of the chamber 17, the front ends of the rails 90 are angled and the front end of each rail 90 has a plate 91 mounted thereacross to form a surface against which a tapered stop 92 (preferably made of Teflon) mounted on the front end of each rail 44 may engage and ramp against to properly align the rails 44 with the rails 90 when the cart 13 is pushed forward toward the chamber 17.

The chamber 17 is fitted with two thermal energy booster apparatuses 93 mounted opposite each other on each side of the interior 83 of the chamber 17 and extending the length of the chamber 17. The thermal energy booster apparatuses 93 preferably are made of corrosion-resistant stainless steel and are designed to withstand the system pressures and temperatures. The thermal energy booster apparatuses 93 provide dry heat to the interior 83 of the chamber 17 to aid in the vaporization of fluids in the chamber 17 and provide a heat source for the dry heat sterilization process of the invention. Preferably, the thermal energy booster apparatuses 93 are plates, which I refer to as Thermal Energy Booster Plates, having a conduit 95 formed therein for carrying steam, such that the apparatuses 93 act like radiators to provide dry radiant heat to the interior 83 of the chamber 17.

Figure 3:
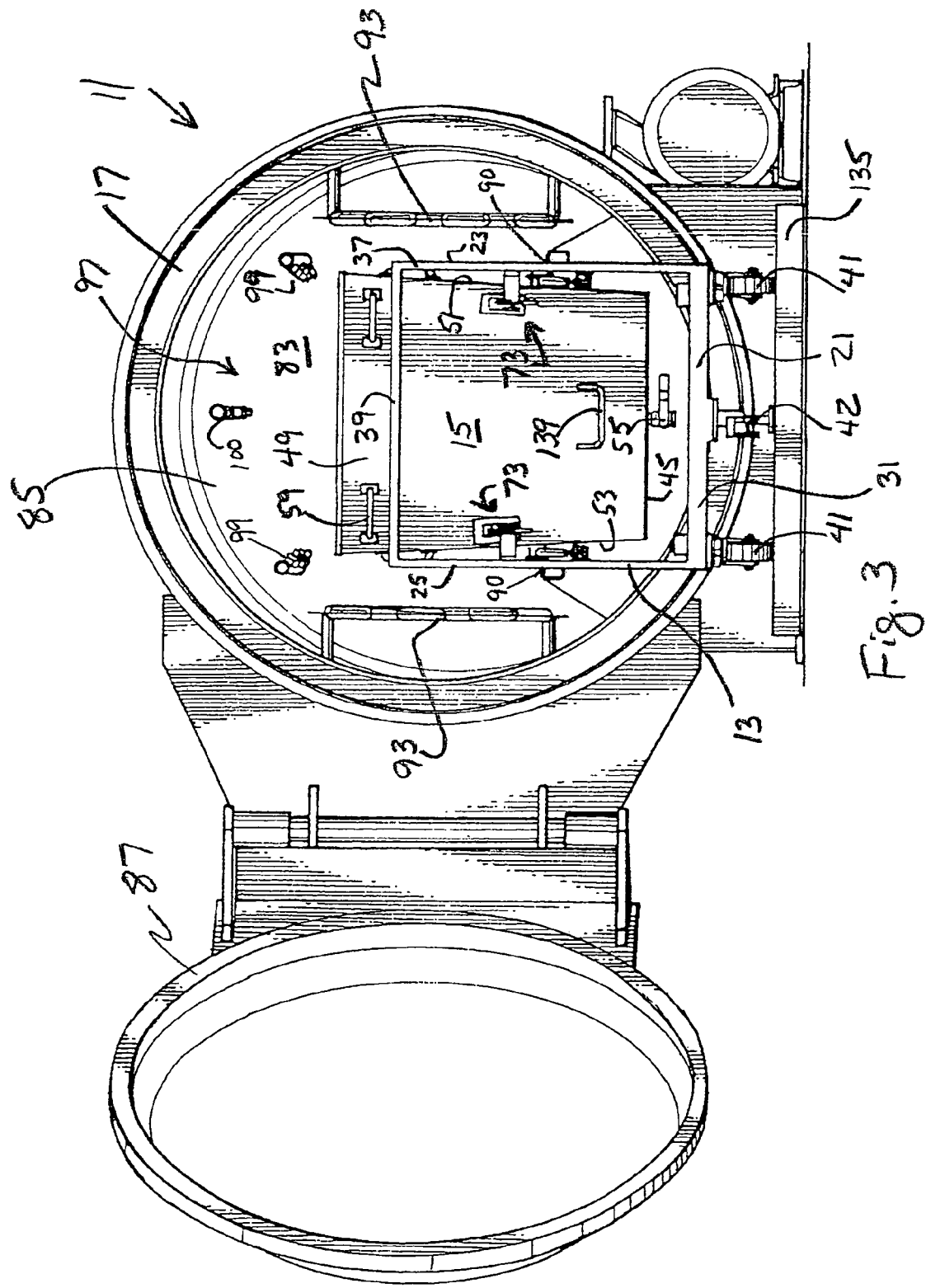
FIG. 3 is an end view of the system of FIGS. 1 and 2, illustrating the interior of the sterilization chamber.
Figure 7:
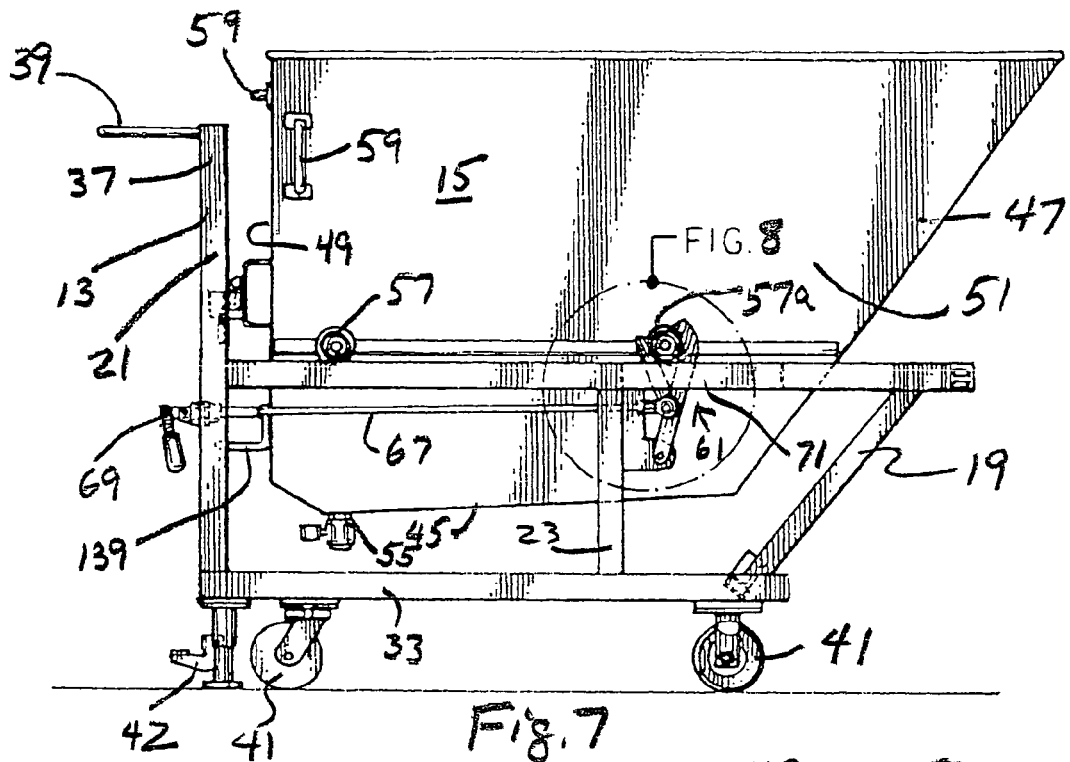
FIG. 7 is a view in side elevation of the cart and the bin of FIGS. 1-3, with the hook arms 63 and 65 of the latching assembly 61 engaged around the front wheels 57a of the bin 15.
Figure 12:
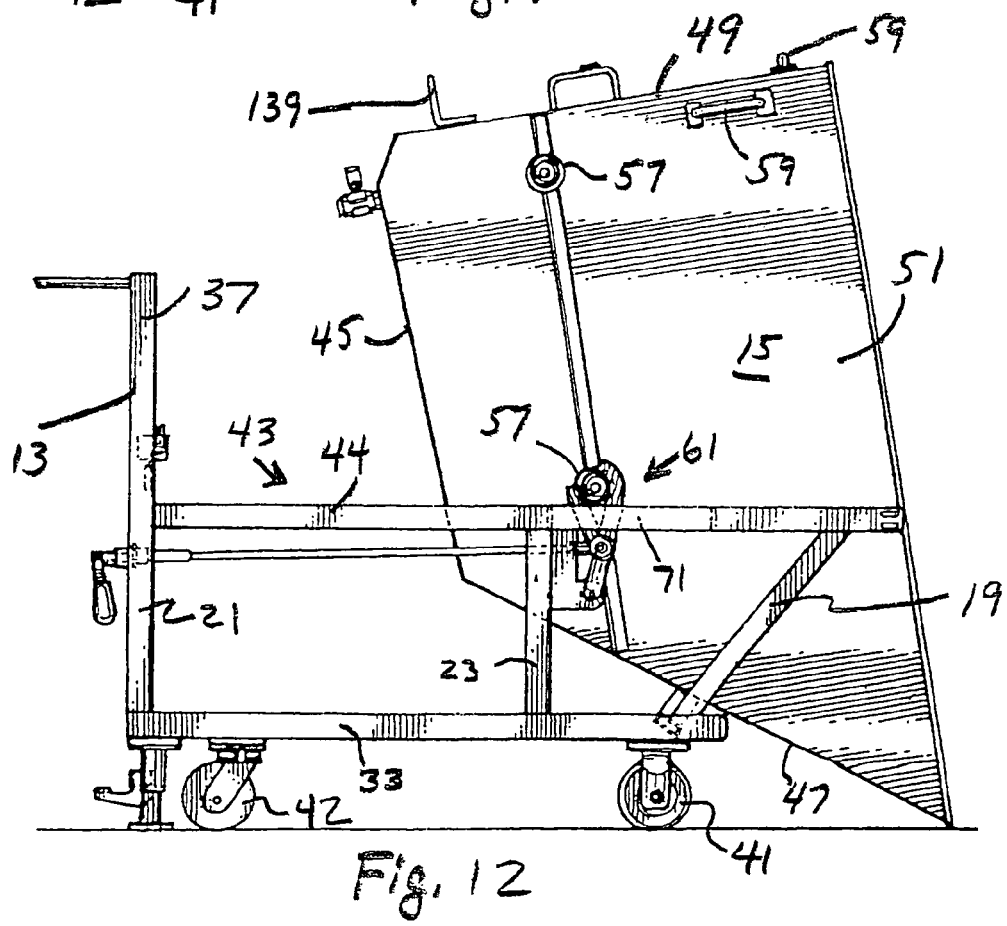
FIG. 12 is a view in side elevation showing the bin 15 being dumped.
Figure 10:
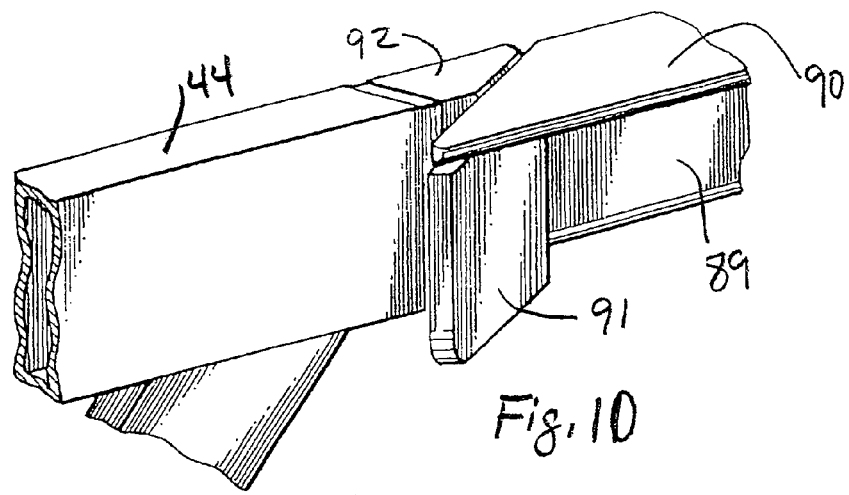
FIG. 10 is an enlarged view of the alignment mechanism shown in the circle 10 of FIG. 1.

As shown in FIGS. 2 and 3, a water spraying assembly 97 is provided to the sterilization chamber 17 for cooling the bin 15 after sterilization and prior to removal of the bin 15 from the sterilization chamber 17. The water spraying assembly 97 includes nozzles 99 mounted in the interior 83 of the sterilization chamber 17 that are aligned to spray cooling water on the outside of the side walls 51 and 53 of the bin 15. The nozzles 99 spray water to cool down the bin 15 after sterilization has occurred and are arranged to do so by spraying the outside of the walls of the bin 15. The nozzles 99 are arranged so as not to get water on the treated, sterilized waste held in the bin 15.

The water spraying assembly 97 also is provided with nozzles 100, which are used together with nozzles 99, when it is desired to spray pressurized water onto the bin 15 (both the exterior and interior sides of the bin walls) to clean and rinse the bin 15. Accordingly, the invention provides for periodic cleaning of the bin 15 in the chamber 17, rather than requiring manual cleaning at a remote location.

A drain valve 101 is connected to the sterilization chamber 17 for liquid to drain from the sterilization chamber 17 when desired.

Figure 13:
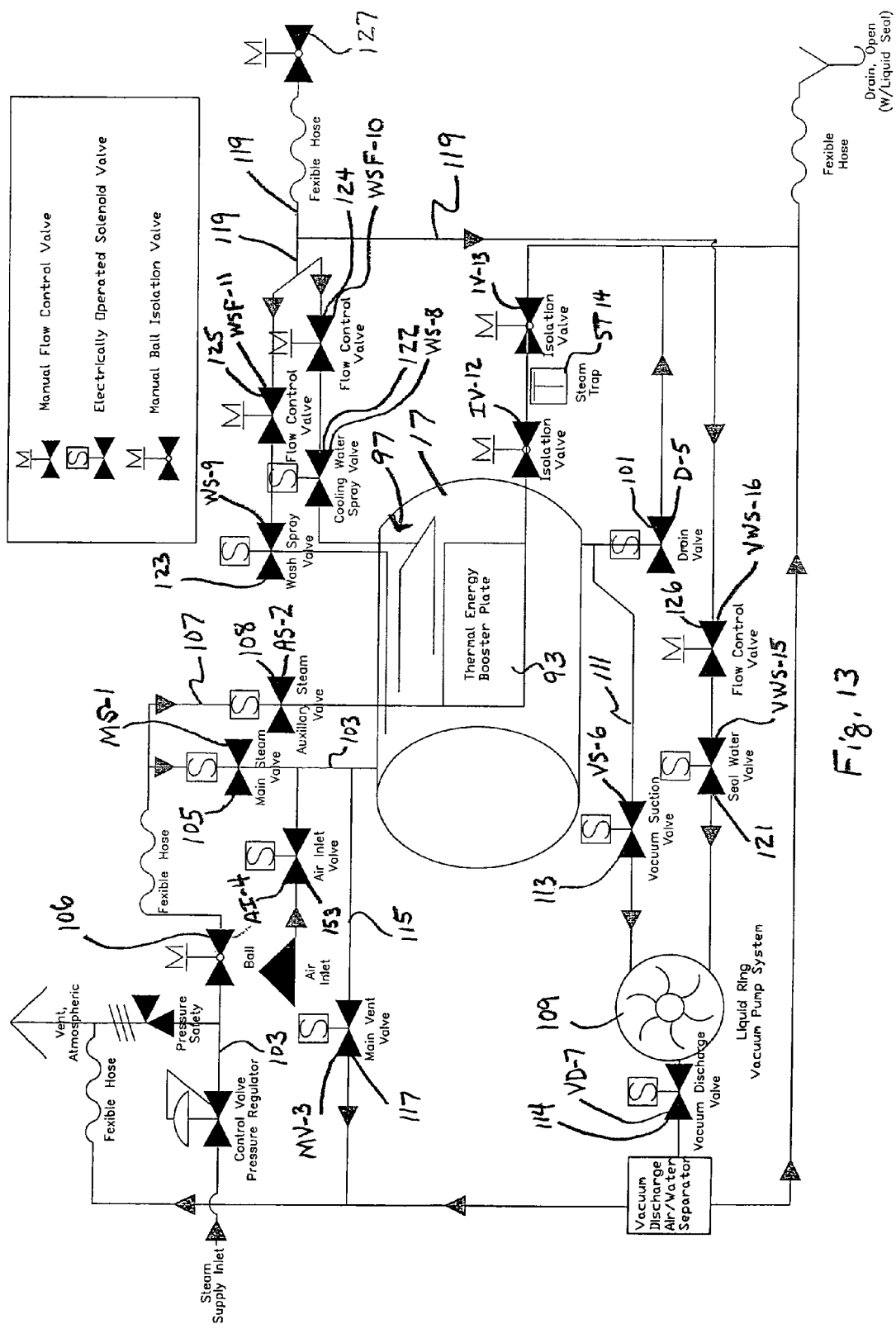
FIG. 13 is a schematic drawing illustrating the steam, vacuum and water systems used in conjunction with the sterilization system of the invention.

As shown schematically in FIG. 13, piping 103 is provided to supply steam, preferably at 15 to 20 psig, to the sterilization chamber 17. A solenoid controlled steam valve 105 (Main Steam Valve MS-1 as referred to in FIGS. 13, 14, and 15a, 15b, and 15c) is provided along the piping 103 to control the flow of steam into the sterilization chamber 17. Piping 107 branches off piping 103 to provide steam to the thermal energy booster apparatuses 93, and a solenoid controlled steam valve 108 (Auxiliary Steam Valve AS-2 as referred to in FIGS. 13, 14, and 15a, 15b, and 15c) is provided along the piping 107 to control the flow of steam into the thermal energy booster apparatuses 93. Preferably, a manual isolation valve 106, preferably a manual ball valve, is provided along the piping 103 upstream from the solenoid steam control valves 105 and 108 as a safety feature. When the sterilization system 11 is not in use, the isolation valve 106 may be manually closed to prevent steam from accidentally flowing into the sterilization chamber 17 if the steam valve 105 opens and to prevent steam from accidentally flowing into the thermal energy booster apparatuses 93 if the steam valve 105 opens.

A vacuum pump 109 is provided for evacuating the sterilization chamber 17 between steam cycles during the sterilization process. The vacuum pump 109 is provided along piping 111. Preferably, the vacuum pump 109 is a single stage, liquid ring pump that uses water as the seal fluid and that is suited as a vapor pump. The vacuum pump 109 preferably is connected to the sterilization chamber 17 through a stainless steel manifold and is isolated by a solenoid-activated vacuum valve 113 (Vacuum Pump Suction Valve VS-6 as referred to in FIGS. 13, 14, and 15a, 15b, and 15c) and a solenoid activated vacuum valve 114 (Vacuum Discharge Valve VD-7 as referenced to in FIGS. 13, 14, and 15a, 15b, and 15c).

Piping 103 includes a vent portion 115 for venting the sterilization chamber 17 to atmosphere, and a valve 117 (Main Vent Valve MV-3 as referred to in FIGS. 13, 14, and 15a, 15b, and 15c), preferably an electro-magnetic solenoid activated valve, is provided along piping vent portion 115 to open and close the vent portion 115.

Piping 119 is provided to supply water, preferably at 30 psig minimum, to the vacuum pump 109 and to the water spraying assembly 97.

A valve 121 (Vacuum Pump Water Seal Valve VWS-15 as referred to in FIGS. 13, 14, and 15a, 15b, and 15c), preferably an electro-magnetic solenoid valve, is provided along the piping 119 to allow the flow of water (to be used as seal fluid) to the vacuum pump 109. Preferably, a manual flow valve 126 (Flow Control Valve VWS-16 as referenced to in FIGS. 13, 14, and 15a, 15b, and 15c) is provided upstream of the valve 121 to control the flow of water to the vacuum pump 109.

A valve 122 (Water Spray Valve WS-8 for cool-down of bin 15 as referred to in FIGS. 13, 14, and 15a, 15b, and 15c), preferably an electro-magnetic solenoid activated valve, is provided along the piping 119 to allow the flow of water to the nozzles 99 of the water spraying assembly 97. Preferably, a manual flow valve 124 (Flow Control Valve WSF-10 as referenced to in FIGS. 13 and 14) is provided upstream of the valve 122 to control the flow of water to the nozzles 99.

A valve 123 (Water Spray Valve WS-9 for washing bin 15 as referred to in FIGS. 13, 14, and 15a, 15b, and 15c), preferably an electro-magnetic solenoid activated valve, is provided along the piping 119 to allow the flow of water to the nozzles 100 of the water spraying assembly 97. Preferably, a manual flow valve 125 (Flow Control Valve WSF-11 as referred to in FIGS. 13 and 14) is provided upstream of the valve 123 to control the flow of water to the nozzles 100.

An isolation valve 127, preferably a manual ball valve, is provided along piping 119 upstream of the valve 121, valve 122, and the valve 123 as a safety feature to be manually closed when the sterilization system 11 is not in use.

Referring to FIG. 2, a programmable logic controller 131 is connected to the system 11 and manages sequential control functions and system interlocks. The controller 131 controls the steam valves 105 and 108, vent valve 117, the drain valve 101, the vacuum valves 113 and 114, the liquid ring and water supply valve 121, the cooling spray valve 122, the wash spray valve 123, and the vacuum pump 109, and it monitors and records process temperature and pressure. The controller 131 is preferably housed in a weather-proof NEMA enclosure.

The system 11 also includes a scale 135 for weighing the items to be sterilized. The weight of the items to be sterilized is inputted into the controller 131, which varies the process times, process temperatures, and process pressures to predetermined settings that correlate to the weight of the items to be sterilized, thereby enabling the system 11 to sterilize varying levels of biological (germ) load, waste mass, and quantities of fluids. Preferably, the scale 135 is linked to the controller 131 such the weight of the items to be sterilized measured by the scale 135 is automatically transmitted to the controller 131, which then varies the process times, process temperatures, and process pressure to predetermined settings that correlate to the weight measured by the scale 135. The matrix that defines how the parametric variables are adjusted has been empirically established using beta-testing of the efficacy of the various process times, various process temperatures, and various process pressures.

A programmable logic controller 131 manages the sequential control, fault, diagnostic and system interlock functions. An onboard interconnected computer provides authorized access to settings, data logging for each cycle, periodic processing statistics and maintenance records. An onboard plain paper printer and data storage device prints a comprehensive single page report for each cycle including pressure and temperature charts and has the capacity to maintain all of the processing and maintenance records for a period of up to seven years. Ethernet capability makes it possible for authorized personnel to remotely view real time processing information, faults and diagnostic information as well as generate periodic processing reports right at their desk. The system is fully automated and features a multi-function operator interface. The interface provides simple cycle selection and start up for the operator. Optionally, the system may be programmed to require operator identification before any function can be activated or any fault condition can be acknowledged or reset. The operator may also view in real time the progress of the process along with the temperature and pressure or vacuum inside the chamber.

As shown in FIG. 4, a removable lid 139 is provided for covering the bin 15. Preferably, the removable lid 139 is made of light-weight plastic and is hinged to provide easy access to the bin 15 without requiring removal of the entire lid 139 from the bin 15. The entire lid 139 is removed prior to the bin 15 being rolled into the sterilization chamber 17 during the sterilization process.

In operation, the cart 13 having the bin 15 secured thereon is used to collect regulated medical waste to be sterilized. The regulated medical waste that is to be sterilized is placed in the bin 15. The lid 139 is preferably used to cover the bin 15 and the medical waste contained therein during collection. The preferred hinged lid 139 shown in the drawings facilitates access to the bin 15 for placement of medical waste therein.

After the medical waste has been collected, the cart 13 with the bin 15 mounted thereon is moved to the sterilization chamber 17, where the lid 139 is removed from the bin 15 and placed aside. Next, with the door 87 of the sterilization chamber 17 opened, the cart 13 is then pushed to the opening 85 of the sterilization chamber 17 so that the tapered stops 92 engage and ramp against the alignment plates 91 to assure that the cart 13 is properly aligned with the opening 85 of the sterilization chamber 17, thereby aligning the rails 44 of the rail assemblies 43 of the cart 13 with the rails 90 of the rail assembly 89 of the sterilization chamber 17.

When the cart 13 has been pushed up against the sterilization chamber 17 with the rails 44 properly aligned with the rails 90, the floor brake 42 is engaged to hold the cart 13 in place.

Then, preferably, the cart 13, with the bin 15 attached thereto and containing the items to be sterilized, is weighed on scale 135 and the weight measured by the scale 135 is transmitted to the controller 131, which determines the weight of the items to be sterilized by subtracting the known weight of the cart 13 and bin 15 from the gross weight measured by the scale 135, and adjusts the process times, the process temperatures, and the process pressures as needed to predetermined settings that correlate to the calculated weight of the items to be sterilized.

Next, the latching members 79 are unlatched from catches 75, and the hook arms 63 and 65 are disengaged from the front wheels 57a, to permit the bin 15 to roll forward on the rails 44. The bin 15 is then rolled on its wheels 57 along the rail 44 from the cart 13 into the interior 83 of the sterilization chamber 17 along the aligned rails 90.

Once the bin 15 has been rolled into the sterilization chamber 17, the floor brake 42 is disengaged and the cart 13 is rolled away from the sterilization chamber 17.

Then, the drain valve 55 of the bin 15 is opened and the door 87 of the sterilization chamber 17 is closed.

The start button on the controller 131 is then pressed to start the sterilization process. First, the controller 131 opens the steam valve 108 (Auxiliary Steam Valve AS-2) to feed steam to the thermal energy booster apparatuses 93 to provide dry radiant heat from the thermal energy booster apparatuses 93 to the interior 83 of the chamber 17. Then, the controller 131 opens the steam valve 105 to permit steam to fill the sterilization chamber 17. The controller 131 closes the vent valve 117 and the drain valve 101 of the sterilization chamber 17 when the sterilization chamber 17 is full of steam. Prior to the closing of the vent valve 117 and the drain valve 101, the air in the sterilization chamber 17 outside the waste container systems (i.e., sharps containers, sealed red plastic bags, etc.) is "gravity" displaced by the steam being fed into the sterilization chamber 17.

A thermocouple is mounted in the interior 83 of the sterilization chamber 17 and is connected to the controller 131 to indicate the temperature inside the interior 83 of the sterilization chamber 17. After 250° Fahrenheit is reach within the interior 83 of the sterilization chamber 17, the controller 131 initiates a hold period to kill all airborne pathogens in the containment systems. Preferably, the hold period is about 5 minutes, but can be adjusted to various time lengths based on the pathogen load factor.

Next, the controller 131 closes the steam valve 105 and then cycles open the vent valve 117 until the pressure in the sterilization chamber 17 goes to zero gauge pressure. The controller 131 then opens drain valve 101 to drain sterile condensate, and the controller 131 then closes the drain valve 101. Next the controller 131 opens valves 121, 113 and 114 and initiates the vacuum pump 109 to draw a vacuum in the sterilization chamber 17 to remove the now sterilized air from the containment systems.

After creating a vacuum withdrawing the air from within the containment systems, the controller 131 stops the vacuum pump 109 and closes the associated valves 113, 114 and 121. The controller 131 then opens steam valve 105 admitting high temperature, high pressure steam commencing the waste sterilization cycle. After a preferred retention period of 45 minutes at or above 250° Fahrenheit (or longer if required by the location, state's regulations etc.), the controller 131 closes steam valve 105, and the controller 131 again cycles open the vent valve 117 until the pressure in the sterilization chamber 17 goes to zero gauge pressure. The controller 131 then opens drain valve 101 to drain sterile condensate, and the controller 131 then closes the drain valve 101.

Next, with the thermal energy booster apparatuses 93 continuing to provide heat to aid in the vaporization of fluids in the chamber 17, the controller 131 opens the valves 113, 114 and 121 and initiates the vacuum pump 109 to draw a vacuum to vaporize the condensate and fluids remaining in the chamber 17. After the waste is dry, the controller 131 shuts off the vacuum pump 109, closes the valves 113, 114 and 121, and closes the steam valve 108 (Auxiliary Steam Valve AS-2). The controller 131 then opens the air inlet valve 153 (Air Inlet Valve AI-4 as referred to in FIGS. 13, 14, and 15a, 15b, and 15c) to break the vacuum in the chamber 17. When the chamber 17 reaches 0 psig, the controller 131 then opens the valves 117 and 101.

At this point, to cool the cart, the controller 131 opens the valve 122 to let cooling water flow to and through the water nozzles 99 of the water spraying assembly 97 to spray cooling water on the outside of the walls 51 and 53 of the bin 15 to cool down the bin 15. Upon the bin 15 having been cooled, the controller 131 closes the valve 122. At this point, the controller 131 signals, preferably by initiating a green light located on the enclosure for the controller 131, that the door 87 may be opened and the bin 15 removed from the sterilization chamber 17.

The door 87 is then opened, the drain valve 55 of the bin 15 is closed, and the cart 13 is again located adjacent to the opening 85 of the sterilization chamber 17 with the tapered stops 92 at the front ends of the rails 44 ramped into contact with the plates 91 at the front ends of the rails 90, thereby aligning the rails 44 of the rail assemblies 43 of the cart 13 with the rails 90 of the rail assembly 89 of the sterilization chamber 17, and with the cart 13 held in place by engaging the floor brake 42 again.

With the cart 13 thus positioned, the bin 15 containing the sterilized items may be rolled from the interior 83 of the sterilization chamber 17 onto the cart 13 along the rail assemblies 43 and 89. After the bin 15 has been fully rolled onto the cart 13, it may then be locked in place on the cart 13 by latching the latching members 79 onto the catches 75 and by engaging the hook arms 63 and 65 around front wheels 57a, thereby securing the bin 15 onto the cart 13.

With the bin 15 secured on the cart 13, the floor brake 42 may be released, thereby permitting the cart 13 to be pulled away from the sterilization chamber 17.

The cart 13 with the bin 15 mounted thereon may be moved to a dump location where the sterilized waste may be dumped into a compactor or other suitable container.

Now, the items that have been sterilized may be dumped from the bin 15 at the dump location. Preferably, the floor brake 42 is first re-applied to hold the cart 13 in position. Next, while maintaining the hook arms 63 and 65 of each latching assembly 61 around the front wheels 57a, the latching members 79 are released from the catches 75 to disengage the rear end portion of the bin 15 from the cart 13 to permit the bin 15 to be pivoted around the front wheels 57a to enable the bin 15 to be tilted forward by lifting the rear end portion of the bin 15 to lower the front end of the bin 15. The rear end portion of the bin 15 is then lifted, preferably using handle grips 59, to tilt the bin 15 forward so the sterilized items slide down the front wall 47 of the bin 15 and out of the bin 15.

Alternatively, the latching members 79 may remain latched onto the catches 75 to secure the rear end portion of the bin 15 on the cart 13, and the cart 13 with the bin 15 secured thereon may be dumped as a cart/bin unit using existing dumping apparatus.

The lid 139 may now be replaced onto the bin 15. The cart 13 with the bin 15 mounted thereon is now ready to be used to gather more medical waste for sterilization.

For exemplary purposes, the inventive method described above is illustrated in FIGS. 15a, 15b, and 15c.

When it is desired to wash the bin 15, the bin 15 is placed inside the chamber 17 and the chamber door 87 is closed. The controller 131 closes valve 153 (Air Inlet Valve AI-4) and opens valve 108 (Ancillary Steam Valve AS-2). The controller 131 then opens drain valve 101 (Drain Valve D-5), opens valve 123 (Water Spray Valve WS-9) and valve 122 (Waterspray Valve WS-8) to spray pressurized water onto the bin 15 from nozzles 99 and 100 to wash the bin 15. Then, the controller 131 closes valves 123 and 122 and permits the water in the chamber 17 to drain from the chamber 17. Next, the controller 131 closes valve 101, closes valve 108, and opens valve 153. After the pressure in the chamber 17 reaches 0 prig and the bin has cooled, the bin 15 is removed from the chamber 17. For exemplary purposes, the washing process is illustrated in FIG. 17.

Turning now to FIG. 18, there is shown an alternative embodiment of the invention in which bin 15' is substituted for bin 15. In this embodiment, the remaining components of system 11 described above remain the same.

Bin 15' in this preferred embodiment of the invention is substantially identical to bin 15, except for its shape, load capacity, and the number of wheels 57 mounted thereon. Bin 15' is substantially box-shaped and has a bottom wall 45', a front wall 47', a rear wall 49', and two side walls 51', 53' extending upwardly from the bottom wall 45'. Preferably, the bin 15' is fabricated from corrosion resistant stainless steel and has a 33⅞ inch width, a 59 inch length, and a height of about 36 inches, with an approximate usable volume of 1.5 cubic yards. The two side walls 51' and 53' of the bin 15 are angled in slightly from top to bottom.

A drain valve 55, preferably a ½ inch ball valve, is connected to the bottom wall 45' near the rear wall 49' of the bin 15' for permitting liquid to drain from the bin 15' when desired.

The bin 15' is provided with wheels 57, including middle wheels 57b, mounted on each side wall 51', 53' of the bin 15'. The hook arms 63 and 65 of the latching assemblies 61 engage the middle wheels 57b when the bin 15' is secured on the cart 13. The wheels 57 are spaced such that the wheels 57 engage the rail assemblies 43 located on the side end portions 23 and 25 of the cart 13 so that the bin 15' may be rolled off the cart 13 along the rails 44 when the bin 15' is being loaded into the sterilization chamber 17 from the cart 13 and so that the bin 15' may be rolled onto the cart 13 along the rails 44 and 90 when the bin 15' is being loaded onto the cart 13 from the sterilization chamber 17 after sterilization.

Handle grips 59 are mounted on the rear wall 49' and on the side walls 51', 53' of the bin 15 to facilitate handling of the bin 15.

Like bin 15, bin 15' is provided with a pair of catches 75 mounted on brackets 77 formed on the rear wall 49' of the bin 15', and these catches 75 interact with latching members 79 mounted on the cart 13 as part of the latching assembly 73 to latch bin 15' onto cart 13 when desired.

In use, bin 15' is used in the same manner as the bin 15, except the bin 15' is dumped using existing dumping apparatus, where the cart 13 with the bin 15' secured thereon by the latching assemblies 61 and 73 is dumped as a cart/bin unit.

Turning now to FIG. 19, there is shown another alternative embodiment of the invention in which a bin 15" is substituted for bin 15. In this embodiment, the remaining components of system 11 described above remain the same.

Bin 15" in this preferred embodiment of the invention. has a bottom wall 45", a front wall 47", a rear wall 49", and two side walls 51", 53" extending upwardly from the bottom wall 45". Bin 15" is substantially identical to bin 15, except for its shape and load capacity, and except that bin 15" does not have a drain valve 55 or handle grips 59 on its rear wall 49". Preferably, the bin 15" is fabricated from corrosion resistant stainless steel and has a 33⅞ inch width, a 59 inch length, with an approximate usable bottom wall surface of about 13.8 square feet.

The bin 15" is provided with wheels 57, including middle wheels 57b, mounted on each side wall 51", 53" of the bin 15". The hook arms 63 and 65 of the latching assemblies 61 engage the middle wheels 57b when the bin 15" is secured on the cart 13. The wheels 57 are spaced such that the wheels 57 engage the rail assemblies 43 located on the side end portions 23 and 25 of the cart 13 so that the bin 15" may be rolled off the cart 13 along the rails 44 when the bin 15" is being loaded into the sterilization chamber 17 from the cart 13 and so that the bin 15" may be rolled onto the cart 13 along the rails 44 and 90 when the bin 15" is being loaded onto the cart 13 from the sterilization chamber 17 after sterilization.

Handle grips 59 are mounted on the side walls 51", 53" of the bin 15" to, facilitate handling of the bin 15".

Like bin 15, bin 15" is provided with a pair of catches 75 mounted on brackets 77 formed on the rear wall 49" of the bin 15", and these catches 75 interact with latching members 79 mounted on the cart 13 as part of the latching assembly 73 to latch bin 15" onto cart 13 when desired.

In use, bin 15" is used in the same manner as the bin 15, except that bin 15" is used in a dry sterilization process of the invention, and the bin 15" is manually unloaded rather than dumped after the sterilization process since the items to be sterilized, such as documents and things, are not destroyed.

Specifically, the paper and/or things to be sterilized is/are collected in the bin 15" that is removably mounted on the cart 13, and the paper and/or things to be sterilized is/are transported using the cart 13 with the bin 15" removably mounted thereon to the sterilization chamber 17. The cart 13 is positioned at the sterilization chamber 17 such that the rails 44 of the cart 13 at the front end portion of the cart 13 abut against and are in alignment with the rails 90 of the sterilization chamber 17. Preferably the paper and/or things to be sterilized is/are then weighed on the scale 135. With the floor brake 42 engaged, the bin 15" is disconnected from the cart 13 and rolled on its wheels 57 from the cart 13 into the sterilization chamber 17 along the aligned rails 44 and 90. Preferably, the controller 131 is used to recognize the weight of the items to be sterilized measured by the scale 135 and to vary process times and process temperatures to predetermine settings that correlate to the weight measured by the scale 135. The sterilization chamber 17 is heated with dry radiant heat generated from the thermal energy booster apparatuses 93 to an effective temperature to sterilize the paper and/or things in the bin and maintain the temperature at or above the effective temperature until sterilization of the paper and/or things has been accomplished. After sterilization has been accomplished, the bin 15" and its contents are allowed to cool. The bin 15" is then removed from the chamber 17 by rolling the bin 15" along the rails 90 from the chamber 17 onto the rails 44 of the cart 13. The bin 15" is re-secured on the cart 13 using latching assemblies 61 and 73, the floor brake 42 is released, and the cart 13 with the bin 15" secured thereto containing the sterilized items therein is moved to where it is desired to unload the sterilized items. The floor brake 42 is then re-applied and the sterilized items are unloaded from the bin 15".

For exemplary purposes, the inventive method described above is illustrated in FIG. 20.

Turning now to FIG. 21, there is shown another embodiment of the invention in which the chamber 17' is substituted for the chamber 17.

Chamber 17' in this preferred embodiment is identical to chamber 17, except that chamber 17' is a double capacity chamber, that is, a chamber having sufficient length to accommodate two bins end to end. The chamber 17' has substantially the same design and construction specifications as chamber 17, except that the rail assembly 89' has a longer length than the rail assembly 89 to accommodate two bins end to end, the water spraying assembly 97' has a longer length than the water spraying assembly 97 to accommodate the length of two bins, and four thermal energy booster apparatuses 93 are mounted in chamber 17' (two on each side of the chamber 17') rather than the two that are mounted in the chamber 17.

Any of bins 15, 15' or 15" may be used in chamber 17' or chamber 17. However, chamber 17' may accommodate two bins at once. Each bin 15, 15', and 15" is provided with a handle 139 on its rear wall 49, 49', 49" to facilitate removal of the bins 15, 15', or 15" from the chamber 17', especially the innermost bin 15, 15', or 15" in the chamber 17' when two bins are used.

Figure 22:
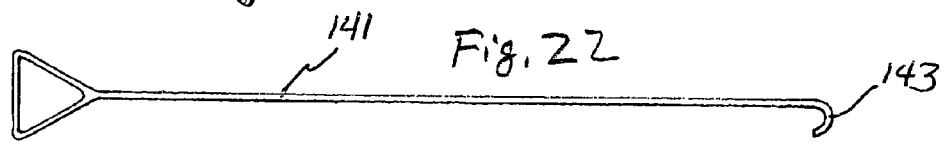
FIG. 22 is a view in elevation of a pole 141 used to pull a bin 15, 15', or 15" from the interior of the chamber 17' shown in FIG. 21.
Figure 8:
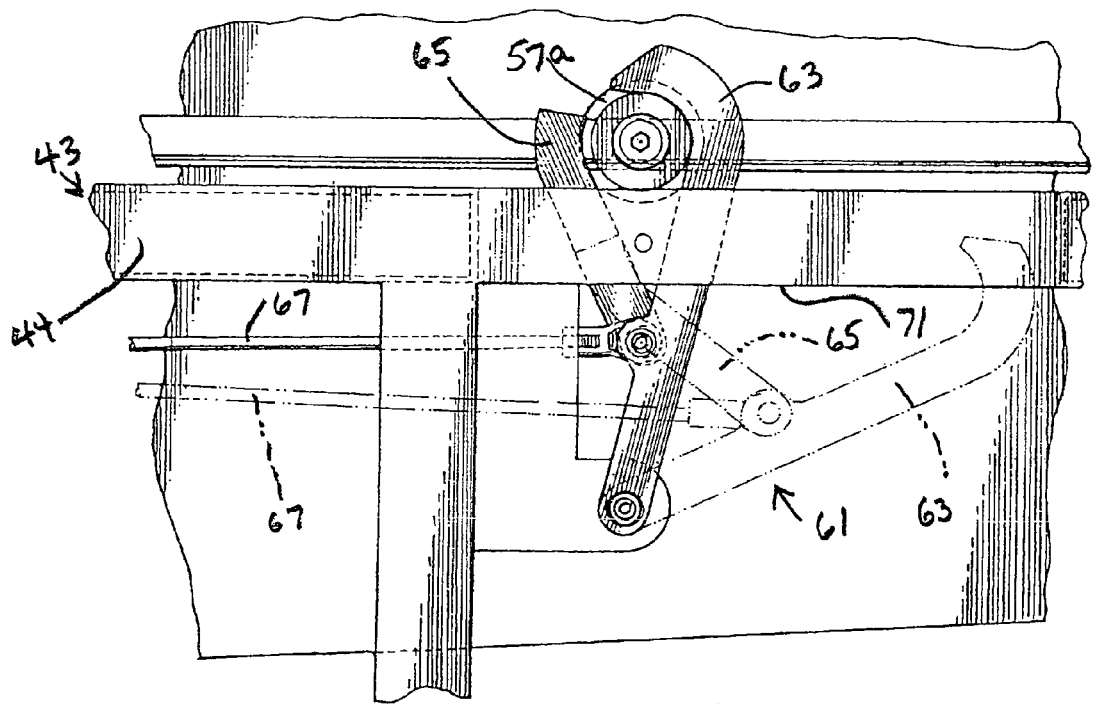
FIG. 8 is an enlarged view of the hook arms 63 and 65 of the latching assembly 61 engaging a front wheel 57a shown in the circle 8 of FIG. 7.

Using a pole 141 having a hook 143 formed at one end portion (FIG. 22), the bin 15, 15', or 15" may be pulled from the chamber 17' by inserting the pole 143 into the chamber 17', hooking the hook 143 onto the handle 139, and then pulling on the pole 141 to pull the bin 15, 15', or 15" from the chamber 17' along the rails 90' of rail assembly 89'.

As is detailed above, the inventive sterilization process in a preferred embodiment uses a combination of steam injection and vacuum to treat potential airborne pathogens, to enhance heat transfer, and to increase system efficacy. The use of vacuum removes residual air and provides and transport mechanism for steam delivery. Sterilization is accomplished using steam at a pressure of 15 psig, which corresponds to an operating temperature of 250° Fahrenheit.

An important characteristic of my inventive sterilization system 11 is management of airborne pathogens. In a preferred embodiment, the sterilization process cycle begins by gravity charging the sterilization chamber 17 with steam, thereby increasing the temperature to the killing temperature for airborne pathogens, then subsequently removing the air from the waste containment systems (i.e., sharps containers, sealed red plastic bags, etc.) which kills airborne pathogens that might otherwise be released through the discharge of the vacuum pump 109.

The sterilization system 11 is preferably used with medical waste containment systems having ventilation means formed therein. Venting the containment systems allows steam to permeate confined volumes of the containment systems and accelerates the heating cycle.

The use of vacuum in combination with dry heat in a preferred embodiment of my invention promotes the vaporization of fluids and the removal of the resultant vapors.

My sterilization system 11 provides a material handling system that accommodates the complete cycle of the processing medical waste, including the collection of medical waste, sterilization of the medical waste, and the transportation and dumping of the treated medical waste from the sterilization unit to the treated sterilized waste facility compactor. The handling system eliminates the need to transfer waste products from a collection cart to the sterilizer, thereby improving pathogen containment. Further, the handling system eliminates the need to transfer treated sterilized waste product from the sterilizer to the plastic/rubber carts for transportation to the hospital's compactor.

The material handling system provided by my invention reduces physical handling of the waste material by hospital personnel thereby reducing the chances of injury to hospital personnel since the waste material need not be physically handled by hospital personnel after it is initially loaded into the bin 15.

The material handling system provided by my invention also provides for sterilization of items, such as paper documents and other things, that are not to be discarded after sterilization.

The invention claimed is:

1. A method of sterilizing regulated medical waste using a steam autoclave that uses high temperature steam greater than 250 degrees Fahrenheit as an agent for sterilization, comprising the steps of
    weighing the regulated medical waste to be sterilized to measure its weight,
    selecting a waste type from a plurality of waste classifications that may be treated by the autoclave, the waste type selected pertaining to the medical waste type to be sterilized,
    automatically varying process times, including residence time that the waste to be sterilized is exposed to steam in the autoclave, process temperatures, and process pressure, including vacuum for negative pressure and steam injection for positive pressure, to predetermined settings that correlate to the selected waste type and to the weight measured during the weighing step, and automatically varying duration of vacuum drawn and steam injection in the autoclave to predetermined settings that correlate to the selected waste type and to the weight measured during the weighing step, and
    sterilizing the regulated medical waste to be sterilized with the autoclave using the predetermined settings that correlate to the selected waste type and to the weight measured during the weighing step.

2. The method of claim 1, the autoclave including a pressure vessel, the pressure vessel having a sterilization chamber for steam sterilization, the sterilizing step including
    placing the medical waste contained in waste containment systems into the sterilization chamber of the autoclave,
    displacing the air in the sterilization chamber with steam,
    heating the sterilization chamber with the steam to an effective temperature for killing all airborne pathogens in the waste containment systems and maintaining the temperature in the sterilization chamber at or above the effective temperature until the airborne pathogens are killed,
    drawing a vacuum in the sterilization chamber after the airborne pathogens in the containment systems have been killed,
    introducing steam into the sterilization chamber again,
    heating the sterilization chamber with the steam to an effective temperature to sterilize the medical waste and maintaining the temperature in the sterilization chamber at or above the effective temperature until the medical waste is sterilized, and
    drawing a vacuum in the sterilization chamber after the medical waste has been sterilized to vaporize condensate.

3. The method of claim 1, the autoclave including a pressure vessel, the pressure vessel having a sterilization chamber for steam sterilization, wherein the sterilization step takes place in the sterilization chamber, and wherein a bin is used for holding the medical waste in the sterilization chamber, the bin having bin walls that form the bin, and further including the step of spraying cooling water from nozzles affixed inside the sterilization chamber on outer surfaces of bin walls for cooling the bin after sterilization.

4. The method of claim 1, wherein the sterilization step takes place in a sterilization chamber of the autoclave, and further including the step of providing steam generated dry radiant heat in the sterilization chamber to vaporize fluids present in the sterilization chamber on the medical waste after sterilization.

5. The method of claim 4,
    the steam generated dry radiant heat being provided from a thermal energy booster plate mounted in the sterilization chamber, the thermal energy booster plate having a conduit formed therein for carrying steam to heat the plate to produce dry radiant heat to radiate from the plate.

6. The method of claim 1, the sterilization step including multiple times both drawing a vacuum in the sterilization chamber and introducing steam to the sterilization chamber.

7. The method of claim 1,
    wherein the sterilization step takes place in a sterilization chamber of the autoclave, and
    wherein a bin is used for holding the medical waste in the sterilization chamber, and
    further including the steps of
    inserting the bin into the sterilization chamber after the medical waste held in the bin has been sterilized and emptied from the bin,
    providing steam generated dry radiant heat in the sterilization chamber to heat the bin,
    spraying pressurized wash water from nozzles mounted in the sterilization chamber onto the bin to wash the bin,
    after the spraying step is completed, drying the bin by continuing to provide steam generated dry radiant heat in the sterilization chamber, and
    after the drying step is completed, discontinuing providing steam generated dry radiant heat in the sterilization chamber and removing the bin from the sterilization chamber for reuse.

8. A sterilization system, comprising
    an autoclave, the autoclave having a sterilization chamber, the chamber having an interior, the chamber having an opening through which access to the interior of the chamber is obtained, and the chamber having the door mounted at the opening for sealingly closing the opening when closed,
    a scale integrated with a control computer for weighing the items to be sterilized, and
    a programmable logic controller controlled by the control computer, the programmable logic controller configured to manage sequential sterilization process steps and configure to automatically vary programmable logic controller set points including process times, including residence time that the waste to be sterilized is exposed to steam in the autoclave, process temperatures, process pressure, including vacuum for negative pressure and steam injection for positive pressure, and duration of vacuum drawn and steam injection in the autoclave, based upon predetermined settings that correlate to a waste type selected from a plurality of waste classifications for treatment by the autoclave that pertains to the medical waste type to be sterilized and to the weight measured by the scale.

9. The sterilization system of claim 8, further including
a bin for holding items to be sterilized, and
a water spraying assembly for cooling the bin after sterilization, the water spraying assembly having nozzles mounted in the interior of the chamber and aligned to spray cooling water on outer walls of the bin.

10. The sterilization system claim 8, further including
a thermal energy booster apparatus mounted in the sterilization chamber for providing steam generated dry radiant heat to the sterilization chamber, the thermal energy booster apparatus having a conduit formed therein for carrying steam to heat the thermal energy booster apparatus to produce dry radiant heat to radiate from the thermal energy booster apparatus.

11. A method of sterilizing things using an autoclave, comprising the steps of
weighing the things to be sterilized to measure their weight,
selecting a type from a plurality of types of things that may be treated by the autoclave, the type selected pertaining to the type of things to be sterilized,
automatically varying process times, process temperatures, and process pressures for sterilizing the things to be sterilized to predetermined settings that correlate to the selected type and to the weight measured during the weighing step, and
sterilizing the things to be sterilized with the autoclave using the predetermined settings that correlate to the selected type and to the weight measured during the weighing step.

12. The method of claim 11, the sterilizing step including
placing the things to be sterilized into a sterilization chamber of the autoclave,
displacing the air in the sterilization chamber with steam,
heating the sterilization chamber with the steam to an effective temperature for killing all airborne pathogens among the things to be sterilized and maintaining the temperature in the sterilization chamber at or above the effective temperature until the airborne pathogens are killed,
drawing a vacuum in the sterilization chamber after the airborne pathogens in the containment systems have been killed,
introducing steam into the sterilization chamber again,
heating the sterilization chamber with the steam to an effective temperature to sterilize the things to be sterilized and maintaining the temperature in the sterilization chamber at or above the effective temperature until the things to be sterilized are sterilized, and
drawing a vacuum in the sterilization chamber after the things to be sterilized have been sterilized to vaporize condensation.

13. The method of claim 12, wherein the sterilization step takes place in a sterilization chamber of the autoclave, and further including the step of providing steam generated dry radiant heat in the sterilization chamber to vaporize fluids present in the sterilization chamber.

14. The method of claim 13,
the steam generated dry radiant heat being provided from a thermal energy booster plate mounted in the sterilization chamber, the thermal energy booster plate having a conduit formed therein for carrying steam to heat the plate to produce dry radiant heat to radiate from the plate.

15. The method of claim 11, wherein the sterilization step takes place in a sterilization chamber of the autoclave, and wherein a bin is used for holding the things to be sterilized in the sterilization chamber, the bin having bin walls that form the bin, and further including the step of spraying cooling water from nozzles affixed inside the sterilization chamber on outer surfaces of bin walls for cooling the bin after sterilization.

16. The method of claim 11, wherein the sterilization step takes place in a sterilization chamber,
the sterilization step comprising heating the things to be sterilized with steam generated dry radiant heat to an effective temperature to sterilize the things to be sterilized and maintaining the temperature at or above the effective temperature until sterilization of the things to be sterilized has been accomplished, by providing thermal energy from a thermal booster apparatus positioned in the sterilization chamber, the thermal energy booster apparatus having a conduit formed therein for carrying steam to heat the thermal energy booster apparatus to produce dry radiant heat to radiate from the thermal energy booster apparatus.

17. A method of treatment for Regulated Medical Waste by an autoclave that is controlled by variable data inputs to a computer programmed to reset a programmable logic controller (PLC) for the distinctive waste characteristics of each individual Regulated Medical Waste load being treated, comprising the steps of
inputting data pertaining to the waste classification of the Regulated Medical Waste to be treated into the computer,
inputting data pertaining to the weight of the waste load of the Regulated Medical Waste being treated into the computer,
using the computer, setting the programmable logic controller (PLC) to predetermined settings that correlate to the data inputted pertaining to the waste classification of the individual Regulated Medical Waste load to be treated,
using the computer, setting the programmable logic controller (PLC) to predetermined settings that correlate to the data inputted pertaining to the weight of the individual Regulated Medical Waste load to be treated, and
treating the individual Regulated Medical Waste load to be treated in the autoclave using the predetermined settings that correlate to the data inputted pertaining to the waste classification of the individual Regulated Medical Waste load to be treated and that correlate to the data inputted pertaining to the weight of the waste load of the Regulated Medical Waste load to be treated to disinfect/sterilized the individual Regulated Medical Waste load,
the individual Regulated Medical Waste load treating step including using high temperature steam greater than 250 degrees Fahrenheit in the autoclave as an agent for disinfection/sterilization.

18. A method of sterilizing things using an autoclave, comprising the steps of
weighing the things be sterilized to measure their weight,
selecting a cycle of treatment by the autoclave from a plurality of cycles of treatment by the autoclave that pertains to the type of things to be sterilized,
automatically varying process times, process temperatures, and process pressures of the autoclave for sterilizing things to predetermined settings that correlate to the cycle of treatment selected that pertains to the type of things to be sterilized and to the weight measured during the weighing step, and
sterilizing the things to be sterilized with the autoclave using the predetermined settings that correlate to the cycle of treatment selected that pertains to the type of things to be sterilized and to the weight measured during the weighing step.

19. The method of claim 18, the sterilizing step including placing the things to be sterilized into a sterilization chamber of the autoclave, displacing the air in the sterilization chamber with steam, heating the sterilization chamber with the steam to an effective temperature for killing all airborne pathogens among the waste and maintaining the temperature in the sterilization chamber at or above the effective temperature until the airborne pathogens are killed, drawing a vacuum in the sterilization chamber after the airborne pathogens in the containment systems have been killed, introducing steam into the sterilization chamber again, heating the sterilization chamber with the steam to an effective temperature to sterilize the things to be sterilized and maintaining the temperature in the sterilization chamber at or above the effective temperature until the things to be sterilized are sterilized, and drawing a vacuum in the sterilization chamber after the things to be sterilized have been sterilized.

20. The method of claim 18, wherein the sterilization step takes place in a sterilization chamber of the autoclave, and wherein a bin is used for holding the things to be sterilized in the sterilization chamber, the bin having bin walls that form the bin, and further including the step of spraying cooling water from nozzles affixed inside the sterilization chamber on outer surfaces of bin walls for cooling the bin after sterilization.

21. The method of claim 18, wherein the sterilization step takes place in a sterilization chamber of the autoclave, and further including the step of providing steam generated dry radiant heat in the sterilization chamber to vaporize fluids present in the sterilization chamber after sterilization.

22. The method of claim 18, the sterilization step including multiple times both drawing a vacuum in the sterilization chamber and introducing steam to the sterilization chamber.

23. The method of claim 18, wherein the sterilization step takes place in a sterilization chamber of the autoclave, and wherein a bin is used for holding the things to be sterilized in the sterilization chamber, and further including the steps of inserting the bin into the sterilization chamber after the things to be sterilized held in the bin have been sterilized and emptied from the bin, providing steam generated dry radiant heat in the sterilization chamber to heat the bin, spraying pressurized wash water from nozzles mounted in the sterilization chamber onto the bin to wash the bin, after the spraying step is completed, drying the bin by continuing to provide steam generated dry radiant heat in the sterilization chamber, and after the drying step is completed, discontinuing providing steam generated dry radiant heat in the sterilization chamber and removing the bin from the sterilization chamber for reuse.

* * * * *